US008963708B2

(12) United States Patent
Chen

(10) Patent No.: US 8,963,708 B2
(45) Date of Patent: Feb. 24, 2015

(54) BREACH DETECTION IN SOLID STRUCTURES

(75) Inventor: Richard D. Y. Chen, Napa, CA (US)

(73) Assignee: Sensurtec, Inc., Napa, CA (US)

( * ) Notice: Subject to any disclaimer, the term of this patent is extended or adjusted under 35 U.S.C. 154(b) by 0 days.

(21) Appl. No.: 13/349,327

(22) Filed: Jan. 12, 2012

(65) Prior Publication Data
US 2013/0281793 A1 Oct. 24, 2013

Related U.S. Application Data

(60) Provisional application No. 61/432,461, filed on Jan. 13, 2011.

(51) Int. Cl.
G08B 21/00 (2006.01)
G08B 1/08 (2006.01)
G08B 23/00 (2006.01)
(Continued)

(52) U.S. Cl.
CPC . A61B 5/74 (2013.01); A61B 5/686 (2013.01); A61F 2/32 (2013.01); A61B 5/076 (2013.01); A61N 1/08 (2013.01); A61N 1/37 (2013.01); A61N 1/37258 (2013.01); A61B 2560/0276 (2013.01); A61F 2002/3067 (2013.01); A61F 2002/488 (2013.01)
USPC .......... 340/540; 340/573.1; 340/539.11; 340/539.12; 600/300; 128/899; 606/192; 623/7; 623/8; 623/23.16; 623/23.67

(58) Field of Classification Search
CPC ............. A61M 5/14276; A61M 2205/3507; A61M 2205/3523; A61M 5/16831; A61M 2205/18; A61M 2205/581; A61M 2205/582; A61M 5/168; A61M 15/02; A61M 16/0051; A61M 1/3663; A61B 5/0031; A61B 2560/0219; A61B 5/0022; A61B 2560/0276; A61B 5/0215; A61B 5/02455; G06F 19/3418; A61N 1/37211
USPC ............. 340/573.1, 539.11, 539.12; 600/300; 128/899; 606/192; 623/7, 8, 23.16, 623/23.67
See application file for complete search history.

(56) References Cited

U.S. PATENT DOCUMENTS 3,046,988 A 7/1962 Moreau et al.
3,055,371 A 9/1962 Kulick
(Continued)

FOREIGN PATENT DOCUMENTS

EP 0103481 A1 3/1984
EP 0246999 A1 11/1987
(Continued)

OTHER PUBLICATIONS

International search report and written opinion dated May 17, 2012 for PCT/US2012/021204.

Primary Examiner — Daniel Wu
Assistant Examiner — Emily C Terrell
(74) Attorney, Agent, or Firm — Wilson Sonsini Goodrich & Rosati

(57) ABSTRACT

An implantable device includes at least one solid structure having an external surface and a volume beneath the surface. One or more of a first conductor or set of conductors is disposed externally and/or internally on or within the structure and an array of elongate electrically conductive elements are disposed radially outwardly within the volume. A breach is detected when a conductive fluid intrudes into the volume through the surface.

22 Claims, 19 Drawing Sheets

(51) Int. Cl.
*A61B 5/00* (2006.01)
*A61B 19/00* (2006.01)
*A61M 29/00* (2006.01)
*A61F 2/52* (2006.01)
*A61F 2/12* (2006.01)
*A61F 2/36* (2006.01)
*A61F 2/32* (2006.01)
*A61B 5/07* (2006.01)
*A61N 1/08* (2006.01)
*A61N 1/37* (2006.01)
*A61N 1/372* (2006.01)
*A61F 2/30* (2006.01)
*A61F 2/48* (2006.01)

(56) References Cited

U.S. PATENT DOCUMENTS

| | | | |
|---|---|---|---|
| 3,934,274 A | 1/1976 | Hartley, Jr. | |
| 4,133,315 A | 1/1979 | Berman et al. | |
| 4,246,893 A | 1/1981 | Berson | |
| 4,416,267 A | 11/1983 | Garren et al. | |
| 4,472,226 A | 9/1984 | Redinger et al. | |
| 4,485,805 A | 12/1984 | Foster, Jr. | |
| 4,501,264 A | 2/1985 | Rockey | |
| 4,607,618 A | 8/1986 | Angelchik | |
| 4,648,383 A | 3/1987 | Angelchik | |
| 4,651,717 A | 3/1987 | Jakubczak | |
| 4,694,827 A | 9/1987 | Weiner et al. | |
| 4,723,893 A | 2/1988 | Kiyooka et al. | |
| 4,739,758 A | 4/1988 | Lai et al. | |
| 4,773,909 A | 9/1988 | Chaglassian | |
| 4,790,848 A | 12/1988 | Cronin | |
| 4,899,747 A | 2/1990 | Garren et al. | |
| 4,908,011 A | 3/1990 | Jacobsen et al. | |
| 5,084,061 A | 1/1992 | Gau et al. | |
| 5,234,454 A | 8/1993 | Bangs | |
| 5,259,399 A | 11/1993 | Brown | |
| 5,383,929 A | 1/1995 | Ledergerber | |
| 5,674,288 A | 10/1997 | Knapp et al. | |
| 5,833,603 A | 11/1998 | Kovacs et al. | |
| 5,993,473 A | 11/1999 | Chan et al. | |
| 6,454,785 B2 | 9/2002 | De Hoyos Garza | |
| 6,579,301 B1 | 6/2003 | Bales et al. | |
| 6,656,194 B1 | 12/2003 | Gannoe et al. | |
| 6,733,512 B2 | 5/2004 | McGhan | |
| 6,736,793 B2 | 5/2004 | Meyer et al. | |
| 6,746,460 B2 | 6/2004 | Gannoe et al. | |
| 6,755,861 B2 | 6/2004 | Nakao | |
| 7,849,751 B2 * | 12/2010 | Clark et al. | 73/768 |
| 2002/0055757 A1 | 5/2002 | Torre et al. | |
| 2002/0128546 A1 * | 9/2002 | Silver | 600/365 |
| 2003/0163197 A1 | 8/2003 | Chen | |
| 2003/0171768 A1 | 9/2003 | McGhan | |
| 2004/0059289 A1 | 3/2004 | Garza Alvarez | |
| 2004/0106899 A1 | 6/2004 | McMichael et al. | |
| 2004/0186502 A1 | 9/2004 | Sampson et al. | |
| 2004/0186503 A1 | 9/2004 | DeLegge | |
| 2005/0149186 A1 * | 7/2005 | Roballey et al. | 623/8 |
| 2006/0047283 A1 * | 3/2006 | Evans et al. | 606/102 |
| 2006/0111632 A1 | 5/2006 | Chen | |
| 2006/0111777 A1 | 5/2006 | Chen | |
| 2006/0200030 A1 | 9/2006 | White et al. | |
| 2007/0089518 A1 * | 4/2007 | Ericson et al. | 73/649 |
| 2009/0005708 A1 * | 1/2009 | Johanson et al. | 600/587 |
| 2009/0012372 A1 | 1/2009 | Burnett et al. | |
| 2009/0157180 A1 * | 6/2009 | Schraga | 623/8 |
| 2009/0254179 A1 | 10/2009 | Burnett | |
| 2009/0326602 A1 * | 12/2009 | Glukhovsky et al. | 607/41 |
| 2010/0331613 A1 | 12/2010 | Centonze et al. | |
| 2011/0077736 A1 * | 3/2011 | Rofougaran | 623/8 |
| 2011/0137413 A1 * | 6/2011 | Osypka | 623/8 |
| 2011/0160616 A1 * | 6/2011 | Stein et al. | 600/587 |
| 2011/0213221 A1 * | 9/2011 | Roche | 600/301 |

FOREIGN PATENT DOCUMENTS

| | | |
|---|---|---|
| GB | 2090747 A | 7/1982 |
| GB | 2139902 A | 11/1984 |
| WO | WO 83/02888 A1 | 9/1983 |
| WO | WO 87/00034 A2 | 1/1987 |
| WO | WO 88/00027 A1 | 1/1988 |
| WO | WO 03/095015 A1 | 11/2003 |

* cited by examiner

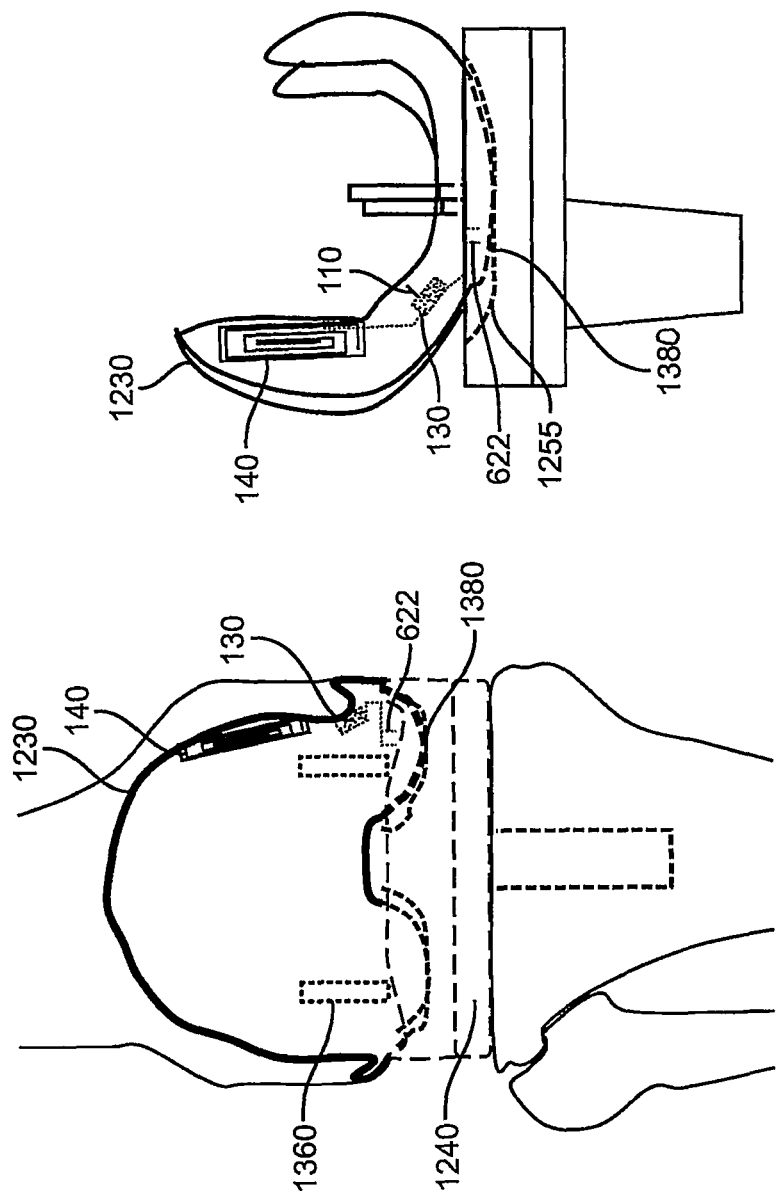

BREACH DETECTION IN SOLID STRUCTURES

CROSS-REFERENCE TO RELATED APPLICATIONS

This application claims the benefit of U.S. Provisional Application No. 61/432,461, filed Jan. 13, 2011, the full disclosure of which is incorporated herein by reference.

BACKGROUND OF THE INVENTION

1. Field of the Invention

The present invention relates generally to medical apparatus and methods. More particularly, the present invention relates to implantable devices and methods and systems for detecting their dysfunction or impending dysfunction.

Implantable medical devices, particularly those indicated for long term use in the human body, are highly regulated and must meet certain safety requirements. It is known that when a device is implanted in the body, the materials forming the cover and structural elements of the device may degrade and fatigue over time. It is also known that improper or excessive handling during implantation could stress the structural integrity of the device. In devices with movable mechanical parts, the wear and tear of the materials in contact with each other could lead to degradation of the surface, the interior volume, and eventually the structural stability of the part itself. Such wear can also release debris particles which in turn can cause harm in a variety of ways including triggering immune reactions which can cause osteolysis and blocking luminal structures which can cause strokes or bowel obstruction. When large enough, the damaged part of the device could shred healthy cells and tissues from red blood corpuscles to bone. Failure of the structural integrity of the device can cause not only dysfunction but severe injury. Often the wear of the device can be moderated or evened by changes in physical activity. Or the impaired part of the device could be replaced without difficulty before the rest of the device is damaged necessitating more extensive revision procedures and rehabilitation. Not only would this enhance safety and reduce costs, the life of the product can be prolonged. Therefore, it would be desirable to detect, to monitor, or to predict such an event and take measures before any irreparable damage to the device or injury to the patient ensues.

Prosthetic devices implanted in numerous locations in the body are prevalent in medical practice and are expected to be of even greater importance than ever before. With medical advances human longevity has increased the population of elderly needing them. Obesity adds further wear and tear on the body. In today's data driven generation, people are more involved in taking care of their own health. The implications are many. Initial, primary therapeutic procedures are performed at younger ages and revision or replacement procedures are increasingly more common. Device statistical lifecycles are no longer satisfactory as patients need information specific to the device implanted in their own body and individualized counseling. Having a device that can be self monitored economically by the patient would be further helpful and reduce overall healthcare costs.

Many devices, such as cardiovascular valves, have parts that are dynamic when performing their function and cannot be stopped for examination. Thus failure prediction and detection often depend on secondary signs, such as errant flow patterns by imaging such as ultrasound. By the time their function is impaired enough to be detected, the wear and tear to the device has already far progressed to require more urgent treatment. Early detection of partial failure through a direct or primary method would enable more accurate diagnosis and better treatment planning.

Other devices suffer repeated or cyclical stresses from deliberate manipulation or secondary body movement. Devices such as insulin or other drug pumps require refilling of the reservoir, typically through a needle. Repeated stabbing in the same location could induce and propagate these defects in the covering that could allow intrusion of body fluids and impair the precisely calibrated functions. Or the refilled fluid could leak through the defects established or propagated by the injecting device. Electronic stimulation devices, such as neurostimulators, and many mechanically restrictive devices, such as lapbands used in bariatric surgery, require fixation of certain critical components to body tissues. As the device and the body tissues are not isolated from motions of the rest of the body, any movement could cause mechanical stress and, over time, fatigue leading to tears or dislocations of the device.

For these reasons, it would be desirable to provide apparatus and methods to detect, to monitor, or predict an actual or potential breach of a surface, layer, or body of an implantable object or device in the body. Prompt removal and/or replacement of such impaired devices or components thereof could avert many, if not all, of the problems associated with failure of such devices. The methods and apparatus would preferably be adaptable for use in many devices without adversely affecting the device's performance or structural integrity. It would be beneficial if the device could be directly examined while functionally deployed in motion without interfering with its performance, even temporarily. It would be further desirable if the breach of the device were detectable to the patient in an easy, rapid, and reliable fashion at home and in other settings away from the doctor and hospital. Additionally, it would be beneficial if the system were able to monitor the device non-invasively on a frequent basis without incurring significant additional cost for each diagnostic event. At least some of these objectives will be met by the inventions described hereinafter.

2. Description of the Background Art

U.S. 2006/0111777 and U.S. 2006/0111632 describe inflatable and rigid implants having embedded conductors utilizing transponders to signal a breach. U.S. Pat. No. 5,833,603 describes an implantable transponder that can be used to detect breach or wear in implantable devices. Breast implants and methods for their use are described in U.S. Pat. Nos. 6,755,861; 5,383,929; 4,790,848; 4,773,909; 4,651,717; 4,472,226; and 3,934,274; and in U.S. Publ. Appln. 2003/163197. Gastric balloons and methods for their use in treating obesity are described in U.S. Pat. Nos. 6,746,460; 6,736,793; 6,733,512; 6,656,194; 6,579,301; 6,454,785; 5,993,473; 5,259,399; 5,234,454; 5,084,061; 4,908,011; 4,899,747; 4,739,758; 4,723,893; 4,694,827; 4,648,383; 4,607,618; 4,501,264; 4,485,805; 4,416,267; 4,246,893; 4,133,315; 3,055,371; and 3,046,988 and in the following publications: US 2004/0186503; US 2004/0186502; US 2004/0106899; US 2004/0059289; US 2003/0171768; US 2002/0055757; WO 03/095015; WO88/00027; WO87/00034; WO83/02888; EP 0103481; EP0246999; GB2090747; and GB2139902.

BRIEF SUMMARY OF THE INVENTION

The present invention provides devices, systems and methods for detecting partial or complete breach of a surface or volume of solid or other non-inflatable structures or components of an implantable device to predict device dysfunction or failure of the structure, component, or device as a whole.

The solid or other non-inflatable structures of the device can be made of any solid material including but not limited to polymers, metals, minerals, ceramics, biologics, and their hybrids. Common examples include articular components of prosthetic joints where the entire volume is solid. Other structures in implantable devices subject to such breach include hermetically sealed rigid-walled enclosures, such as those of implantable defibrillators or neurostimulators, or reservoirs, such as those in implanted insulin or drug pumps, where the volume includes other parts of the device whether gas, liquid, or solid.

Typically the solid structures are subject to breach in areas where there is extensive contact between the device and body tissues or with an external object or between different parts of the device. If the device is manipulated periodically, the area of wear and tear is at the site of stress and fatigue of the manipulation. While the implementation of these systems and methods will be described in detail in connection with orthopedic joints, it will be appreciated that the principles may be applied to other non-inflatable prostheses. The systems of the present invention are incorporated into at least a portion of the surface, layer, or thickness of the non-inflated prosthesis and provide for the emission or transmission of a detectable electronic signal upon breach or partial breach of the same. As used hereinafter, the term "breach" will refer to any partial or full penetration of a surface, layer, or thickness of a structure, or other mechanical disruption which could initiate or lead to the contact of heretofore unexposed device materials with surrounding tissues or body fluids.

The signal emission system of the present invention preferably comprises a signaling circuit having one or more components which become exposed to an exterior or interior environment surrounding or within the prosthesis upon breach or partial breach of the surface, layer, or thickness, wherein such exposure enables, disables, energizes, discharges, and/or changes a signal which is emitted by the system. In particular, the breach will typically close an open region within the signaling circuit to cause, enable, disable, or alter the signal emission.

In a first embodiment, the component of the signaling circuit will generate electrical current when exposed to a body fluid by the breach. In such cases, the generated electrical current can power an unpowered transmission component to emit the signal. Alternatively, the power can alter a signal which has already been continuously or periodically emitted by the signaling circuit. In the latter case, the signaling circuit may require a separate source of energy, such as a battery or circuit components which can be placed on either side of the surface, layer, or thickness so that they are always exposed to fluids to provide for current generation. Devices near parts of the body engaged in movement may utilize piezoelectricity to power the circuit. Optionally, the current can throw a switch irreversibly, i.e., entered into memory, so that its altered state can be detected at a later time.

Alternatively, the circuit components may include spaced-apart conductors which are electrically coupled to the signaling circuit to "close" the signaling circuit to permit current flow when exposed to a body fluid in a breach. In the exemplary embodiments described below, the detection portion of a conductor acting as a probe comprise elongate elements embedded beneath the surface, layer, or thickness of the structure in the location subject to breach with an axis oriented toward the direction of the breach. As used hereinafter, the embedded "conductor" or "probe" refers to the detecting element including, if present, a cover that electrically insulates it from surrounding tissues or body fluids. In this unexposed and electrically isolated position, the probe conducts no current and is electrically inactive. A breach through the surface, layer, or thickness will expose and electrically activate the otherwise isolated probe and provide a channel for the intruding electrically conductive bodily fluids bridging the probe and other conductors. The coupling of the spaced-apart conductors may also cause, alter, or enable a signal emission to alert the patient of the breach or potential breach. The probes can have any one of a variety of shapes or a combination of them to fit the geometry of the structure or the contour of its surface, layer, or thickness and match the geometry of the breach. A single conductor can expand at the distal end, branch out into a multi-pronged configuration, or run in a continuous loop configuration in order to cover a wide area subject to breach to minimize potential disruption to the integrity of the structure. Alternatively, when disposed in a material that is resistant to delamination, the conductor can be shaped in a planar configuration, such as a mesh or a continuous plate, to expand the coverage area of detection. Alternatively, the conductor could be made of a material, such as a polymer or metal, in a three dimensional framework that supports the integrity or stability of the structure. The shallowest sections of the embedded probes can be situated in various locations, preferably near portions of the structure where the most wear and tear is anticipated to enhance sensitivity and reliability of the detection. Conductors separately coupled to the logic circuit can be embedded at different distances from a surface, layer or thickness to detect not only the breach but the extent of it through the volume. They can be separately embedded in different components or sections of them to distinguish the location of the breach. The breadth of the coverage area, the density of probes, and/or the alignment of the probes could be correlated to the seriousness of the breach to minimize the potential that such a breach is missed.

In a preferred embodiment, the signaling circuit will comprise a passive transponder and antenna which are adapted to be powered and interrogated by an external reader. Such transponder circuitry may conveniently be provided by using common radio frequency identification (RFID) circuitry where the transponder and tuned antenna are disposed on or within the prosthesis and connected to remaining portions of the signaling circuit. For example, by connecting the transponder circuitry to "open" conductors which may be closed in the presence of body fluids, the signal transmitted by the transponder upon interrogation by an external reader may be altered. Thus, the patient or medical professional may interrogate the prosthesis and determine whether or not the prosthesis remains intact or a potential breach exists. This is a particularly preferred approach since it allows the user to determine that the transponder circuitry is functional even when a breach has not occurred. In passive circuits where the antenna derive power from incoming radiofrequency signals, the antenna is preferably fixated in a radio frequency privileged location relatively in parallel to the surface of the overlying tissues and/or skin. In this fashion, the plane of the antenna can be orthogonal to the radiofrequency vector in order to maximize radio frequency induction and signal strength. If there is radiofrequency interference from materials nearby, the antenna and/or the circuit will have shielding in the substrate or encased to minimize this effect. To minimize interference even further, the circuitry may be separated from the antenna with the sensitive portions fixated to privileged sites on the device or to the surrounding tissue.

The present invention further provides methods for signaling breach of a surface, layer, or thickness of a structure in a prosthesis. Usually, a wireless signal emission comprises closing a circuit when the surface, layer, or thickness is at least partially breached or generating an electrical current when the surface, layer, or thickness is at least partially breached. The particular signaling circuits and transmission modes have been described above in connection with the methods of the present invention.

The signaling system of the present invention can be designed to function in a variety of algorithms to notify the patient in a simple, unequivocal fashion. For example, in a toggle algorithm, the transmitter is either on in the static state or preferably off in order to reduce the need for power. Upon direct contact with the body fluids and or device contents, the conductors cause the transmitter to turn the signal off or preferably on to be able to send a wireless signal on a continuous basis. The wireless signal or lack thereof is recognized by the detector to notify the patient that the integrity of the device is compromised. Optionally, the conductors can cause a switch to be thrown irreversibly so that its altered state in the memory can be detected at a later time. Optionally, the conductors can cause a switch to be thrown so that other functions of the device are enabled.

Alternatively, the algorithm could be based on time, amplitude, frequency, or some other parameter. For example, the transmitter may be enabled to emit a wireless signal at a predetermined time interval in its static state. The detector recognizes the length of the interval as normal and the existence of the signal as the system in working order. Upon direct contact with the body secretions or device contents by the conductors, the transmitter is enabled to send the same signal at different time intervals or a different signal, which is recognized by the detector to notify the patient that the integrity of the device is compromised. The lack of a signal is recognized by the detector to notify the patient of a detection system malfunction and potential compromise of the integrity of the device.

Optionally, more than one probe or more than one type of probe may be placed internally in different parts or components in the device so that the particular part or component which failed may be identified based on which probe was activated. The transmitter would send different signals for the receiver to display the source of the failure. Optionally, they can be separately embedded in different locations of the same part. Diagnostics amongst the various parts or sections can be easily differentiated with the RFID codes assigned to each part or section. Optionally, probes could be coupled to detect, identify, and/or monitor the cause of the breach, especially in the situation where the material of the structure is subject to a breach by certain chemical or biological agents which may or may not normally be present in the environment. Optionally, two or more probes could be coupled to detect or monitor the extent of the breach in another parameter value. For example, wear and tear often result in the shedding of small debris particles. The detectable presence of these particles, particularly if they have intrinsic or contain ingredients that have electromagnetic properties, and the concentration of them in the surrounding body fluids could be monitored by the coupled probes thereby giving an indication of the site of the debris and the volume of the wear. Optionally, probes activated by the breach could serve as a composite for imaging the location, extent, and depth of the breach. The data from the probes can be plotted on a map to visualize the projections.

The probe is a three dimensional conductor disposed in the material directly underneath the surface, layer, or thickness subject to breach. Embedded in this position, the conductor is directly behind the surface, layer, or thickness in the advancing path of the breach into the structure. Exposing the conductor, therefore, is ipso facto evidence of the breach penetrating through the surface, layer, or thickness overlying the conductor. Depending on the configuration, the conductor can be situated to detect breaches in multiple sides of the structure and from multiple directions. The most sensitive embodiment is planar, such as a fine mesh, lattice, or continuous film of the detection material embedded in the material or in between layers of the materials of the structure. In general, such a configuration optimizes the performance of the system in detecting failures early. If the site of the tear or rupture cannot be predicted, the probe would be unlikely to miss detecting the breach by covering the entire device, as discussed in commonly owned prior patent publications US 2006/0111777 and US 2006/011632, the full disclosures of which are incorporated herein by reference.

A continuous film, mesh, or lattice may be preferred for inflatable or fillable devices where the site of breach is unpredictable and complete failure can result from a very small breach. However, for some non-inflated structures or devices, a continuous film, mesh, or lattice may not be required or even ideal. Most non-inflatable devices do not fail from pinpoint breaches but later from the propagation of them. In orthopedic prostheses, the areas of stress and fatigue are often well identified and circumscribed. For example, in prosthetic orthopedic joints certain structures and parts of them suffer the brunt of the various forces from load bearing. These include but are not limited to compression, dispersion, shear, rotation, friction, and combinations of any of them. Motility usually involves repetitive and cyclical movements of certain body parts. Consequently, particular areas on the articular surfaces suffer the most from these forces and are the most susceptible to degrade and eventually break down from wear and tear. Moreover, the wear and tear is not uniform, layer by layer, because articular surfaces do not experience fixed directional forces applied evenly. This is exacerbated with dedicated sports activities although the particular areas affected are specific for the sport. For others, such as cardiovascular valves, the leaflet edges encounter the most stress from cycles of opening and closing. For devices fixated to body tissues, repetitive and cyclical forces from normal body movements exert strain on particular areas on certain structures. The breaches on these fixation structures, such as locking mechanisms and anchors, again can start at an edge or corner and propagate inward or across the structure. Such mechanisms do not have to have sudden failure to cause a meaningful effect. Mere loosening of a functional part, such as in a lap band, could be the difference between therapeutic success and failure.

A continuous film or lattice could even be disadvantageous for non-inflatable and non-fillable devices. For many, such an embodiment embedded as a layer may actually weaken the structure subject to breach. Corrosion of the device can start in several ways. It could begin as a small crack or tear into the surface or deep in the layer of a load bearing area from a compressive force. Or the surface could begin to pit from friction and shear due to repetitive lateral and rotational movements. Thereafter, shards or small layers of the material are abraded off the protruding edges. As the breach progresses into the volume, the exposed materials continue to erode and wide pits result. If the structure has convexities, they can shear and flatten. This is a continuing material science problem in the design of orthopedic implants for product longevity. Metal and plastic parts are typically titanium or cobalt-chromium alloys and ultra high molecular weight polyethylene, respectively, to balance the needs for strength, flexibility, lubricity, and shape retention. In some instances, synthetic ceramics are also used for their special properties. Surface hardening processes from sintering to special coatings are common. Incorporating the conductors, and if needed, its insulation, as additional planes or layers into different materials introduces surface-to-surface adhesion and differential shear resistance among other problems that could increase susceptibility to propagation of wear and tear and sudden failure. If there is any chemical or biological corrosion, it could travel along the natural plane in the interface between different materials. Therefore, such a planar configuration could even result in accelerated degradation, especially through deformation or delamination.

Given the lower sensitivities required and the non-uniform wear and tear characteristics in certain non-inflatable structures, a probe configuration with minimal potential to change the performance or durability of the structure is desirable. In the preferred embodiment, it is a three dimensional array or arrangement of one or more elongate elements embedded beneath the surface, layer, or thickness subject to breach as described in greater detail below and the accompanying figures. The detecting portions of the probe project from deeper levels in the volume and end at predetermined distances from the surface, layer or thickness. From the surface, an array of points and/or broken lines or curves at predetermined depths is presented to detect the breach. Such an embodiment is minimally disruptive to the overall integrity of the structure while allowing configurations that can maintain coverage of the detection to a wider area.

The probe material could be made of any biocompatible metal, polymer, gel, fiber, particle, ingredient, or combination thereof, with or without any coating or particle impregnation that can generate an electrical charge or enable flow of electric current when in contact with the body fluids or device contents. For example, an electrical charge could be generated from a non-toxic chemical reaction when the elongate element exposed underneath a tear comes in contact with the body secretions. Flow of electric current could be enabled when two ends of an electric circuit hitherto physically separated by electrically non-conductive material in the covering or a structural element of the device are in contact with electrolytes in the body secretions when the intervening electrically non-conductive material is compromised. For example, a charged elongate element is embedded in the core material separate from the ground probe on the external surface of the device. When the elongate element is exposed to the electrolytes in the body fluids in the event of a tear, the circuit is closed. Alternatively, the charged and ground probes could be physically adjacent but electrically separate from each other in the material of the structure and both exposed to body fluids by a breach. Preferred materials include non-corrosive, biocompatible metals and elastomers, inks, or the like which contain electrically conductive particles. They can be rigid or non-rigid. To minimize effects on the material properties and performance characteristics of the structure, it is preferably in the same class of materials or has compatible physical and/or chemical properties as the surrounding materials in the structure subject to breach. So long as the materials of which the elongate element is made are in electrical contact, they can be in any physical composition, even including but not limited to loosely compacted particles or suspensions such as gels. In these alternatives, they can readily assume an altered shape if the structure can deform prior to a breach. If the conductor material is more durable than the material surrounding it, the conductor could even be designed by one skilled in the art to serve an extra function as reinforcement for the structure itself.

Optionally, a conductor material is selected for its intrinsic biochemical effect. For example, silver and gold have natural anti-infectious and anti-inflammatory properties, respectively. Embedded in the structure, the conductor materials are released in doses depending on the magnitude of the breach. Optionally, the probes can be designed by one skilled in the art to function as carriers for biochemical agents, which are eluted and/or activated when exposed by the wear and tear. For example, antibiotics could be delivered to fight infectious organisms or anti-inflammatory agents, such as corticosteroids, to moderate inflammatory responses. Should these agents be electrically non-conductive, they could be incorporated in the insulating cover for the elongate element. Shielded by the intact structure, these agents would lie in waiting for the moment the structure is breached. Given that the release in a breach is immediate and localized, very small amounts of the agents could be effective in controlling these complications early in the process, often far before they become symptomatic. Worn off with the debris of the structure itself, these agents travel with the debris like chaperones. Instead of selecting the materials for their therapeutic value, the materials may be selected for their properties for diagnostic value. For example, the materials could facilitate diagnosis and monitoring for their radio or sono contrast, luminescence, or other chemical or physical properties. Once a breach has been detected, the extent of the distribution and the load of the debris can be imaged non-invasively by readily available radiographic or sonographic equipment. Again, should these agents be electrically non-conductive, they could be incorporated in the insulating cover for the elongate element.

The conductive elongate element in the assembly can be in various configurations to suit the detection criteria and match the contour of the surface, layer, or thickness subject to breach and the geometry of the breach. In its most basic form, the elongate element is a simple cylinder of conductive material. Optionally, it is tapered at the distal end to be minimally disruptive to the structure nearer the surface, layer, or thickness subject to breach. If the material of the structure in which it is embedded is electrically conductive, the elongate element is insulated such that the entire element is of a cylinder or cone in shape. In this configuration, the probe presents a conductive point at the desired depth to detect the breach. This may be sufficiently sensitive if the breach is expected to assume the shape of a shallow and wide depression from shearing and abrasion. Optionally, the conductor is a loop or coil to widen the coverage area or to detect widening breach trajectories. In this configuration, detection of a linear split is enhanced since such a breach could easily miss a point but is likely to extend across and expose a portion of the loop. The coil can be uniform in diameter of a cylinder or has the overall geometry to match the expected path of the breach. For example, an inverted cone might be preferred in a breach that has a small entry but propagates widely deep beneath a surface, layer, or thickness, especially one that has been processed to increase durability. Optionally, the loop can spread out in an expanded pattern within a thickness constituting a patterned conductive line to detect an incoming breach. Optionally, a conductor comprises branches of individual elongate elements arrayed or arranged in a multipronged formation presenting an array of points to detect the breach and the main branches much further behind to minimize the potential disruption to the physical integrity of the structure. These prongs can approach the surface, layer, or thickness at any angle, be in a staggered formation, and/or crisscross each other. Whether the surface, layer, or thickness is flat, convex, or concave, the above configurations or a combination of them could be embedded at suitable depths and densities to detect the existence and extent of the breach. In these configurations, the points or discontinuous lines that end at each uniform distance from the surface, layer, or thickness constitute a line or plane that is parallel to the surface, layer, or thickness.

For surfaces, layers, or thicknesses with complex contours or silhouettes with mixed flats, protuberances, and indentations, it may be problematic to embed precisely the elongate element conductors at uniform depths and/or densities amongst the peaks and valleys of structure or to incorporate multiple conductors without threatening the integrity of the structure. In this situation, the conductive elongate element could be configured as a continuous loop following such contours or silhouettes such that conductive points or broken lines are presented at a uniform distance from such surface, layer, or thickness to detect the breach. Certain portions of the elongate conductor can project out and others depress in to vary the placement of the conductive line within a thickness. The shallowest or detecting sections of the embedded probes can be situated in various locations, preferably near portions of the structure where the most wear and tear is anticipated to enhance sensitivity and reliability of the detection. Such a configuration enables monitoring a large, prescribed area or a specific structural feature with a single conductor. Optionally, the continuous loop following such contours or silhouettes can present conductive points or discontinuous lines or curves at different distances from such surface, layer, or thickness to match the relative probabilities or importance of breaches at different locations.

Regardless of the geometry of the three dimensional formation of the assembled elongate elements, at least one major axis of the configuration is aimed toward the direction of the breach. Usually, this is the axis in alignment with the detection portion of the probe projecting toward the direction of the breach. Typically for a flat surface, layer, or thickness, the axis is the longitudinal which is oriented orthogonal to the surface, layer, or thickness. For a simple convex or concave surface, layer, or thickness this axis is perpendicular or at an angle to the tangential plane depending on the tolerances in manufacturing, impact on the structural integrity, and/or differences in performance characteristics. Where the contour of the surface, layer, or thickness is complex requiring a continuous loop or coil, the preferred axis is the radial intersecting the tangential plane. In this instance, the shallower portions of the conductor project to and are oriented to the contour. Alternatively, if the trajectory of the breach branches out, for example in a cylindrical structure, the radial axis may be directed inward any branch in propagation.

The conductive probes, with or without insulation, can be incorporated into the non-inflatable devices in a variety of manufacturing processes well known to those skilled in the arts. For example, for types of technologies such as casting or molding, the preformed conductor can be placed in the mold at the exact distance from the surface, layer, or thickness and precision casted or molded together with the surrounding core materials to form the structure. Or a bore for the probe can be casted, for example, using the lost wax method. For material removal and forming types of technologies, the component can be precision machined by a computer numerical controlled tool, preferably from behind the surface, layer, or thickness, to form bores or shaped spaces for fixating the conductor. In this direction of machining the component, the surface, layer, or thickness to be monitored would be preserved as a pristine, continuous barrier for the breach. In addition, sources of abrasion or breach, such as any physical deformities or imperfections left behind by machining from the front and any sealing or fixation method, would be obviated. For accretion manufacturing technologies, the conductor can be built into the original substrate or the built part can be machined as above. In the former, for example, the conductor and/or its fixation is held in place as a node and the material of the structure is injected onto and around it from different directions or layer by layer to build up the desired three dimensional structure. If the material is a biologic, the surface of the conductor with its insulation could be engineered to have adhesive properties for the aggregation of the cellular components and growth of the tissue. In the latter, as in the other manufacturing processes, once the bore for the conductor is formed, the conductor can be placed and fixated onto the structure by a variety of processes depending on the material. If it is a solid, the conductor can be inserted directly into the bore and fixated. Alternatively, the bore can be filled with a conductive fluid or paste and then, if needed, transformed into a solid by a variety of means known to those skilled in the art, for example, heat or ultraviolet light curing. The conductor can be uninsulated if the material of the structure is electrically non-conductive. If the material of the structure is conductive, insulation can be preformed over the conductor or placed in the bore prior to introducing the conductor. However, whether the structure material is conductive or not, the conductor is preferably surrounded by insulation along its length to the circuit to form a continuously insulated and electrically isolated appendage prior to placement. In this fashion, there would be no seam that could be poorly sealed or opened after deployment for body fluids to intrude and cause the circuit to send a false positive signal of a breach of the structure. Because of the various axes along which the elongate elements of the conductor are embedded in the structure and potentially tortuous bore, precise machining may be challenging. In this situation, the component can be constructed in three steps. A housing, such as a shaped plug, containing the conductor is first constructed as a male member by any of the processes described above. The component is then precision machined as the female member, preferably from behind the surface, layer, or thickness to hollow out the correspondingly shaped cavity to receive the plug. The plug can be inserted and fixated through a variety of means, including but not limited to mechanical, chemical, physical, or hybrid technologies known to those skilled in the art.

Typically, the component will need to undergo finishing processes. They range from mechanical processes such as polishing to remove imperfections to chemical processes such as coating and sintering to harden the surface. So long as the process does not involve hostile conditions for the conductor assembly and circuitry, the component can be finished with installed conductor. In most situations, however, it will be preferable to complete the surface finishing process before installing the conductor. The treated surfaces can simply be protected during the component assembly. The entire circuitry could be further attached, encased, or hermetically sealed to the assembled component in protective material to form one solid piece, if needed.

The transmitter in the circuit can be a simple wireless signal generator triggered by an electric current or preferably a transponder using the well-established RFID technology, i.e., produces a wireless signal when triggered by an interrogating signal. The electric charge generated or the electric current enabled by the probe in contact with the body fluids or device contents enables the transmitter to emit or causes it to emit a wireless signal. Typically, the transponder is powered by the interrogating radiofrequency signal so that no power source of its own is required. Alternatively, the transmitter could be powered internally by a micro battery or externally by induction. Alternatively, power can be generated by a chemical reaction or piezoelectricity from surrounding body tissues. The circuitry is placed on a substrate which may include shielding to protect it from electromagnetic interference. For protection from degradation by an acidic and electrolyte solution and become potentially toxic, the transmitter or transponder circuit is encased in a highly resistant material, such as silicone rubber, glass, polycarbonate, or stainless steel. The transmitter or transponder circuit can be placed in the interior or on the exterior, preferably away from an area of mechanical stress and electromagnetic interference. The antenna can be placed in a separate radiofrequency privileged location from the circuit but is preferably in an orientation that is most sensitive in sending and receiving signals through body tissue overlying the device. The circuitry and any of its parts may be mechanically fixated to preferred sites on the device or to the tissue in a variety of means known to those skilled in the art. Many of the above teachings are exemplified in the embodiments of the invention in the detailed descriptions of the inventions below.

The wireless signal from the transmitter is recognized by a detector external to the body. The detector could be simply a receiver tuned to the transmitter's signal or, preferably, a combination of both a transmitter of a signal to interrogate the transponder and a receiver to distinguish the different signals from the transponder. The detector is preferably powered by batteries and portable enough to be handheld, worn on a band or belt, or can be placed conveniently near a place where the patient visits often or spends most of his time. Upon receiving a signal that a breach has occurred, the detector will alert the patient to seek medical assistance or alert medical professionals directly through other devices, such as Bluetooth linked to an autodial telephone. The alarm could be auditory, such as beeping sounds, visual, such as flashing LED's or a LCD display, sensory, such as vibrations, or preferably a combination of any or all of the above.

Optionally, the detector could have different auditory, visual, sensory, or different combinations to identify the source of the detected breach, especially with more than one probe or more than one type of probe. For example, LED's of different colors or different sounds could be used. The alarm could further indicate the seriousness of the breach. For example, when multiple probes detect a breach, the volume of the alarm would increase to a higher level. Upon receiving a signal indicating a dysfunction or impending dysfunction of the device, the patient would seek prompt medical care for the timely replacement of the impaired part or component before serious complications. Optionally, the signals indicating the breach from the probes could be compiled into an image to show the location, extent, and depth of the breach.

BRIEF DESCRIPTION OF THE DRAWINGS

FIGS. 13A-13B illustrate a knee prosthesis having the breach detection system of the present invention incorporated in the femoral component.

DETAILED DESCRIPTION OF THE INVENTION

Figure 1C:
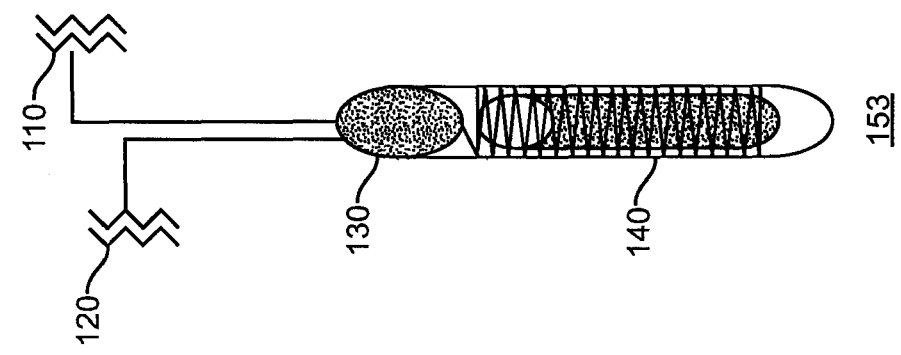
FIGS. 1A-C illustrate the radiofrequency circuitry in three configurations of the breach detection system of the present invention.
Figure 1B:
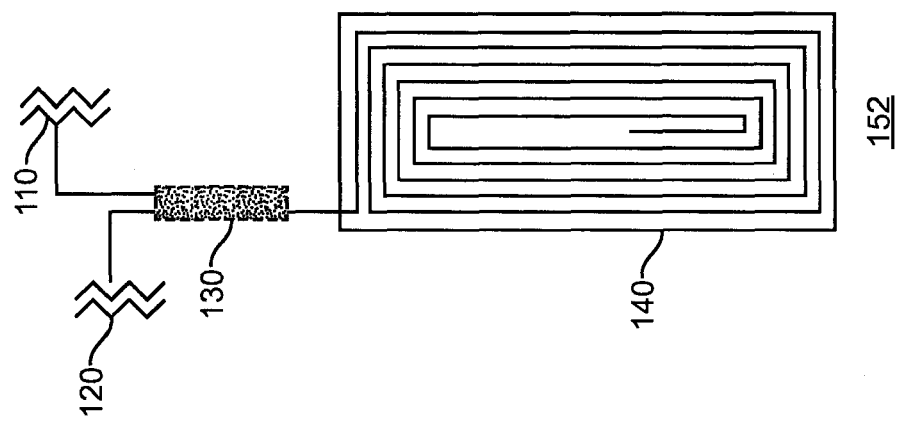
Figure 1A:
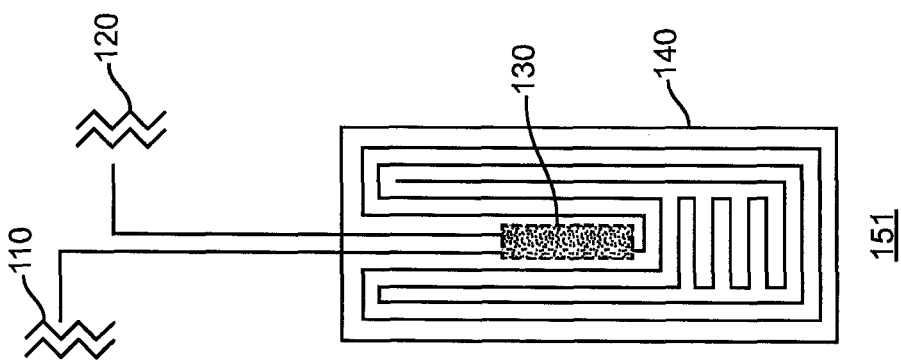
Figure 2E:
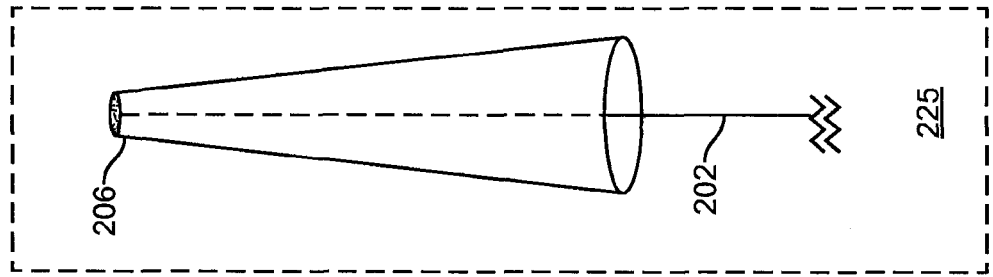
FIGS. 2A-2E illustrate the various configurations of the detecting portion of the second conductor as an elongate element.
Figure 2D:
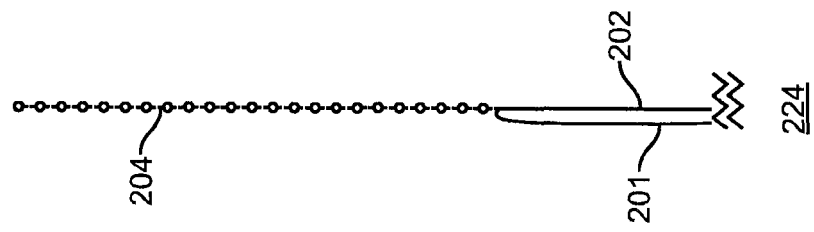
Figure 2C:
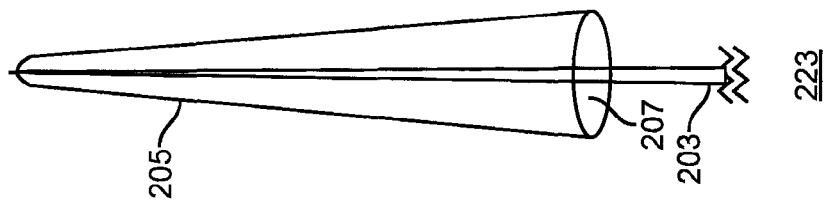
Figure 2B:
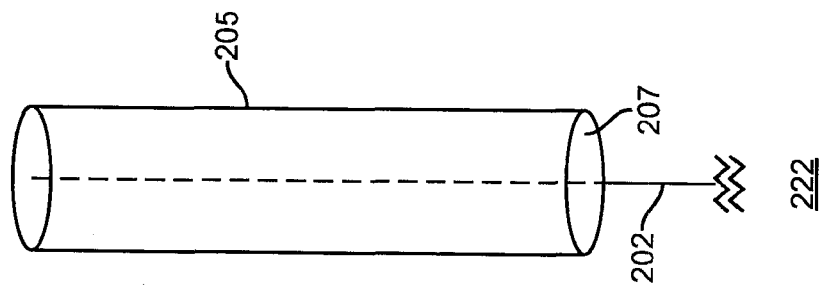
Figure 2A:

Referring now to FIGS. 1A-1C, the radiofrequency circuitry of the device is shown in three configurations, each with four major parts, a first conductor 110, a second conductor 120 (a distal end for detection shown in figures below in more detail), a logic circuit 130, and an antenna 140. The logic circuit 130, unless split into distinct parts, for the descriptive purposes here includes the transmitter and transponder. Conductors 110 and 120 are electrically isolated from each other until a breach exposing the conductor 120 to an electrically conductive fluid intruding into said breach bridges them. In circuitry 151, the logic circuit 130 is on the same substrate as the antenna 140. In circuitry 152, the logic circuit 130 is fixed on another substrate apart from the antenna 140 to accommodate design requirements for size and location, esp. to enhance sensitivity, specificity, or robustness. In circuitry 153, the logic circuitry 130 and a ferrite core antenna 140 is fixed inside a hermetically sealed capsule. It will be obvious to an ordinary person skilled in the art that the circuit could be split further in parts on separate substrates to satisfy design requirements. In passive circuits where the antenna derive power from incoming radiofrequency signals, the antenna is fixated relatively in parallel to the surface of the overlying skin. In this fashion, the plane of the antenna can be orthogonal to the radiofrequency vector in order to maximize capture of radiofrequency energy. The radiofrequency reception can be also be enhanced, such as shown with a ferrite core antenna. Conductor 110 is shown as a single lead wire but can be in any form or shape (not shown here), including the variety of configurations as the conductor 120 below, or electrically coupled to other conducting materials so long as it is electrically exposed to an electrically conductive fluid when the device is implanted in a body or in the event of a breach. Conductors 110 and 120 are shown here in their proximal link to the logic circuit 130 and the double hashed lines indicate the linkage to the distal detecting portion of the conductors.

FIGS. 2A-2E show the distal detecting portion of the second conductor as an elongate element in various configurations. In these and all of the following configurations, should any material be incorporated for enhancement, such as pharmacologic therapeutic or diagnostic agents, whether in the conductor or its insulation, it is not shown separately but represented within the whole. The second conductor 221 is a simple cylinder containing a core of conductive material 202 or a combination of such materials 202. The conductor can be a bare wire if the device material surrounding it has sufficient impedance to electrical conduction. The overall shape of the second conductor 205 including the conducting material 202 and the optional insulating or fixating material 207 surrounding it can be in any elongate form, here shown as a cylinder in conductor 222 or a cone in conductor 223. Conductor 203 is shown in a tapered configuration. In conductor 224, the first conductor 201 is adjacent to the second conductor 202 with insulating material in the middle separating them. At their distal portions, the conductors can be side-by-side, wrapped around each other, loop one around the other, one concentric to the other or form a double helix formation. These close proximity configurations of the first and second conductors 204 is particularly advantageous in specific situations where the first conductor must also be unexposed electrically or, for example, detecting a breach that would expose both conductors simultaneously is desired. If not shown in later figures, this configuration of both the first and second conductors located next to each other may be assumed by figures of only the second conductor. In conductor 225, the shape at the tip forming the frontline of the detection may be enlarged or enhanced with a plate, lattice, film of conductive material. In this figure and in subsequent figures, the double hashed lines indicate the linkage to the logic circuit 130 in FIG. 1.

Figure 3:
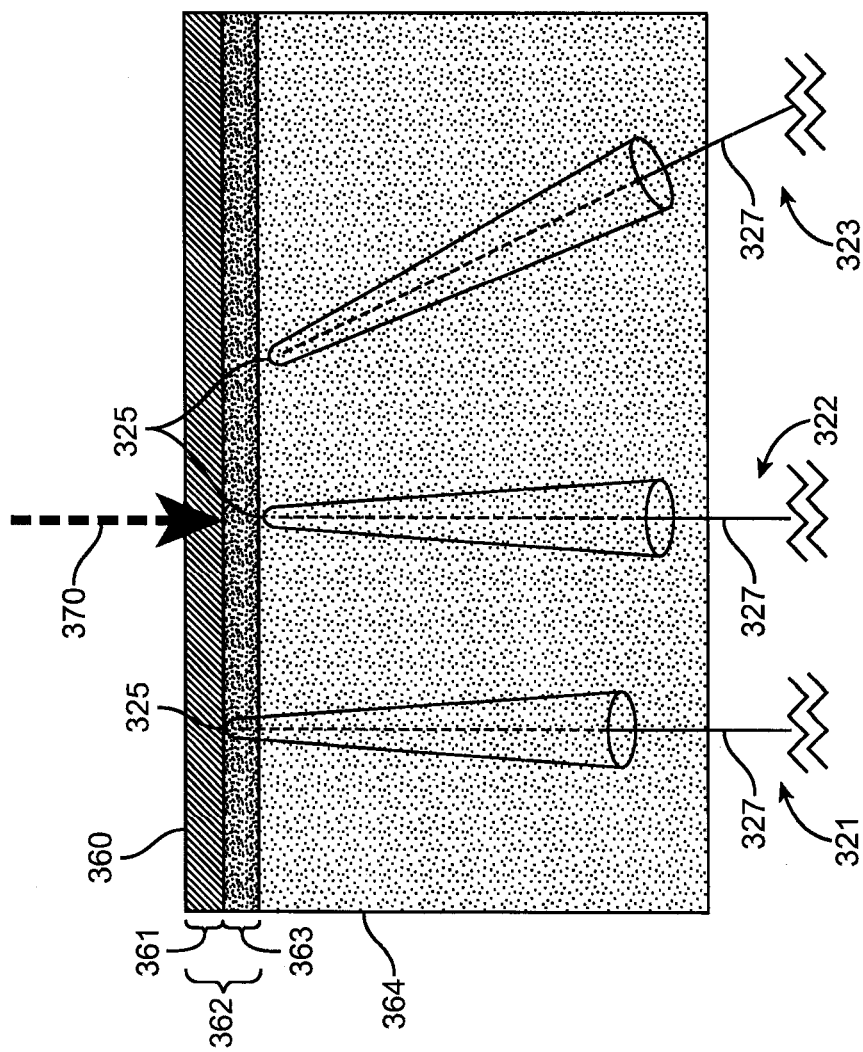
FIG. 3 illustrates the orientation of the detecting portion of the second conductor as an elongate element to the direction of the breach.
Figure 4:
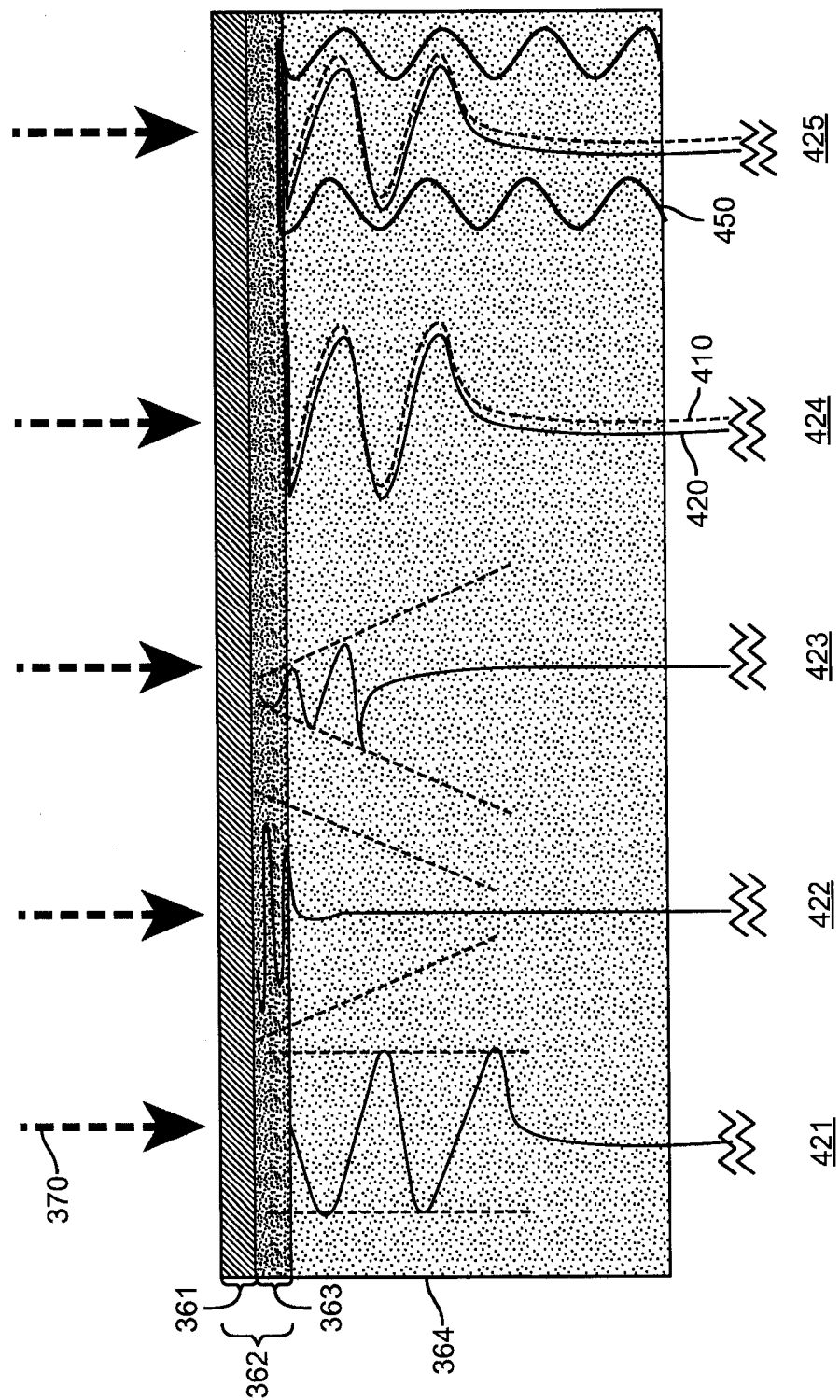
FIG. 4 illustrates an alternative configuration of the elongate element and an example of the method of embedding the elongate element in the material behind the surface, layer, or thickness in the direction of the breach.
Figure 5A:
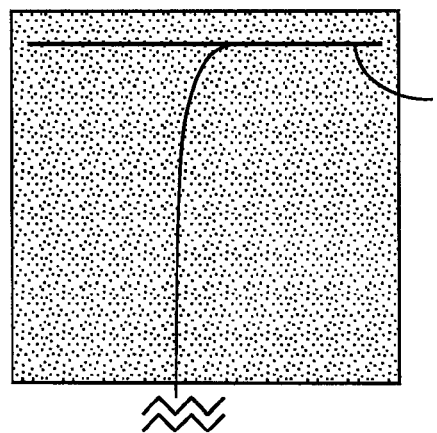
FIGS. 5A-5D illustrate additional configurations of the elongate element where the detection portion of the second conductor is spread out in an expanded pattern to cover a wider area and increase the sensitivity.
Figure 5C:
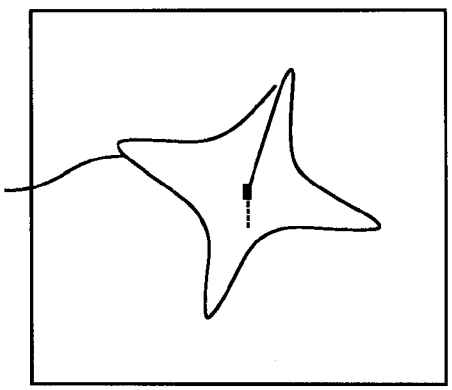
Figure 5B:
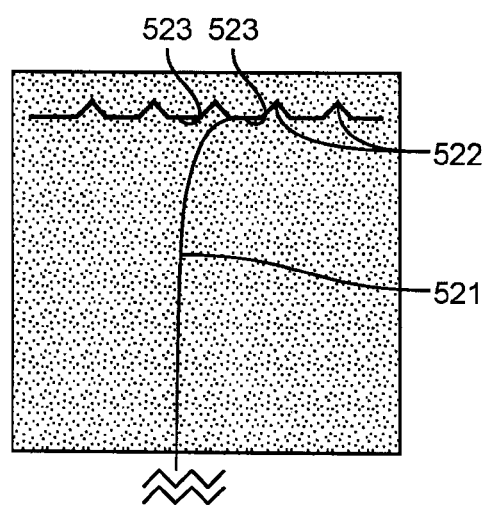
Figure 5D:
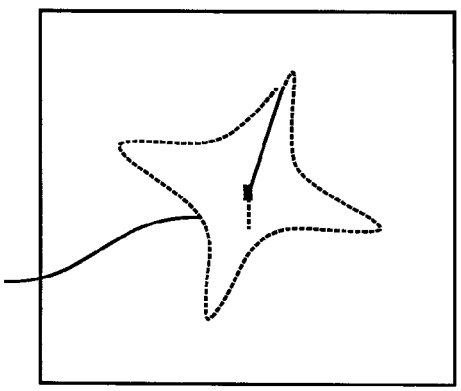

FIG. 3 shows the detection portion of the second conductor as an elongate element with a longitudinal axis oriented toward the direction of a breach. As described in FIG. 2 above, the overall shape may be in any elongate form, here depicted as a cone. The surface, layer, or thickness to be breached is depicted as full or total in 362 or as partial in two layers 361 and 363. Each surface, layer, or thickness while depicted as separate may themselves be made of thicknesses of different materials or is made of the same material as the core 364. Thicknesses 361 and 363 could even represent the processed surface of a structure made from a uniform material through a variety of technologies by one skilled in the art to increase durability. The conductors 321, 322, and 323 are embedded in the core material 364 beneath the exposed outermost surface 360 extending toward and into the surface, layer, or thickness for a fixed distance. The direction and path of the breach is shown as 370 and the conductors are disposed at the interface or plane between the surface, layer, or thickness subject to breach and the layer or thickness of the material underneath it. In this location, the conductors are directly behind the layer or thickness and in front of the core material in the path of the breach. In conductor 321, the detection tip 325 closest to the outermost surface extend through layer 363 and end at the partial thickness 361 to detect a partial breach and in conductor 322, at the full thickness to detect a complete breach. It will be appreciated that the depths of the breach can thus be detected by a number of embedded conductors with tips ending at predetermined levels. The conductor is oriented toward the direction of the anticipated breach with the longitudinal axis perpendicular in conductors 321 and 322 and slanted at an acute angle in conductor 323. Regardless of the angle of approach, it is readily seen that the longitudinal axis of the elongate element intersects the plane of the surface, layer, or thickness subject to breach. Note that the surface 362 may be exposed to an interior and direction of the breach may be from an interior toward an exterior but the conductors are oriented to intercept the breach.

FIG. 3 also illustrates how the elongate elements 321, 322, and 323 intersect a planar region of the implant at different angles, typically between 60° (323) and 90° (321).

FIGS. 2A-2E show the distal detecting portion of the second conductor as an elongate element in various configurations. In these and all of the following configurations, should any material be incorporated for enhancement, such as pharmacologic therapeutic or diagnostic agents, whether in the conductor or its insulation, it is not shown separately but represented within the whole. The second conductor 221 is a simple cylinder containing a core of conductive material 202 or a combination of such materials 202. The conductor can be a bare wire if the device material surrounding it has sufficient impedance to electrical conduction. The overall shape of the second conductor 205 including the conducting material 202 and the optional insulating or fixating material 207 surrounding it can be in any elongate form, here shown as a cylinder in conductor 222 or a cone in conductor 223. Conductor 203 is shown in a tapered configuration. In conductor 224, the first conductor 201 is adjacent to the second conductor 202 with insulating material in the middle separating them. At their distal portions, the conductors can be side-by-side, wrapped around each other, loop one around the other, one concentric to the other or form a double helix formation. These close proximity configurations of the first and second conductors 204 is particularly advantageous in specific situations where the first conductor must also be unexposed electrically or, for example, detecting a breach that would expose both conductors simultaneously is desired. If not shown in later figures, this configuration of both the first and second conductors located next to each other may be assumed by figures of only the second conductor. In conductor 225, the shape at the tip 206 forming the frontline of the detection may be enlarged or enhanced with a plate, lattice, film of conductive material. In this figure and in subsequent figures, the double hashed lines indicate the linkage to the logic circuit 130 in FIG. 1.

FIG. 3 shows the detection portion of the second conductor as an elongate element with a longitudinal axis 327 oriented toward the direction of a breach. As described in FIG. 2 above, the overall shape may be in any elongate form, here depicted as a cone. The surface, layer, or thickness to be breached is depicted as full or total in 362 or as partial in two layers 361 and 363. Each surface, layer, or thickness while depicted as separate may themselves be made of thicknesses of different materials or is made of the same material as the core 364. Thicknesses 361 and 363 could even represent the processed surface of a structure made from a uniform material through a variety of technologies by one skilled in the art to increase durability. The conductors 321, 322, and 323 are embedded in the core material 364 beneath the exposed outermost surface 360 extending toward and into the surface, layer, or thickness for a fixed distance. The direction and path of the breach is shown as 370 and the conductors are disposed at the interface or plane between the surface, layer, or thickness subject to breach and the layer or thickness of the material underneath it. In this location, the conductors are directly behind the layer or thickness and in front of the core material in the path of the breach. In conductor 321, the detection tip 325 closest to the outermost surface extend through layer 363 and end at the partial thickness 361 to detect a partial breach and in conductor 322, at the full thickness to detect a complete breach. It will be appreciated that the depths of the breach can thus be detected by a number of embedded conductors with tips ending at predetermined levels. The conductor is oriented toward the direction of the anticipated breach with the longitudinal axis perpendicular in conductors 321 and 322 and slanted at an acute angle in conductor 323.

Figure 6A:
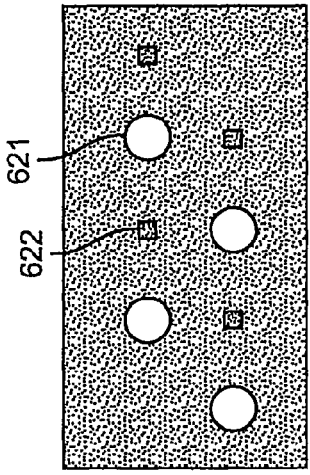
FIGS. 6A-6D illustrate further configurations of the second conductor where two or more elongate elements are combined and coupled in a multipronged formation aiming toward the direction of the breach.
Figure 6B:
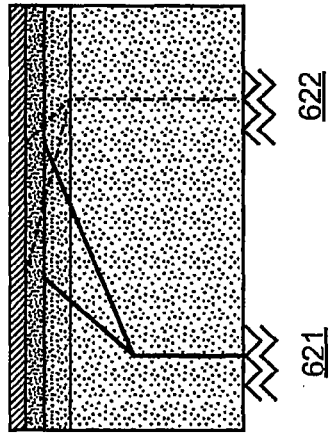
Figure 6C:
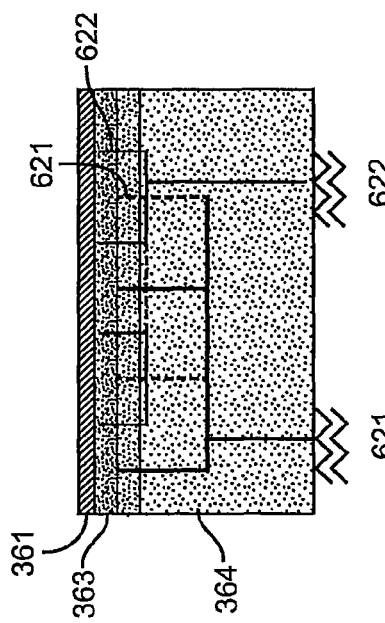
Figure 6D:
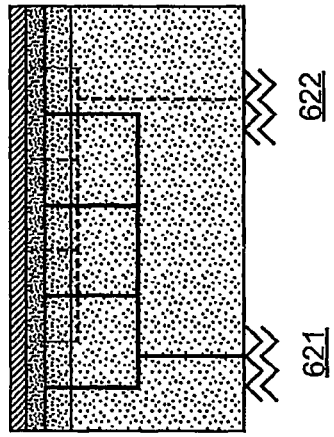

FIGS. 6A-6D show yet another configuration of the second conductor where two or more elongate elements are assembled and coupled in a multipronged formation pointing toward the direction of the breach. In FIG. 6A, Conductors 621 and 622 have branches ending at layer 363 and 361, respectively. The prongs of the two conductors are arranged in a staggered array, as shown in a top view FIG. 6B, thus enabling detection coverage over a wider area of a partial and a full thickness breach. A configuration where the branches of two conductors 621 and 622 are crisscrossed is shown in cross sectional views in FIG. 6C and, rotated 90 degrees, in FIG. 6D. If desired, the staggered arrangement can be produced with branches of different lengths. The prongs may be uniform in shape or a combination of different shapes as depicted in the earlier figures above.

Figure 7B:
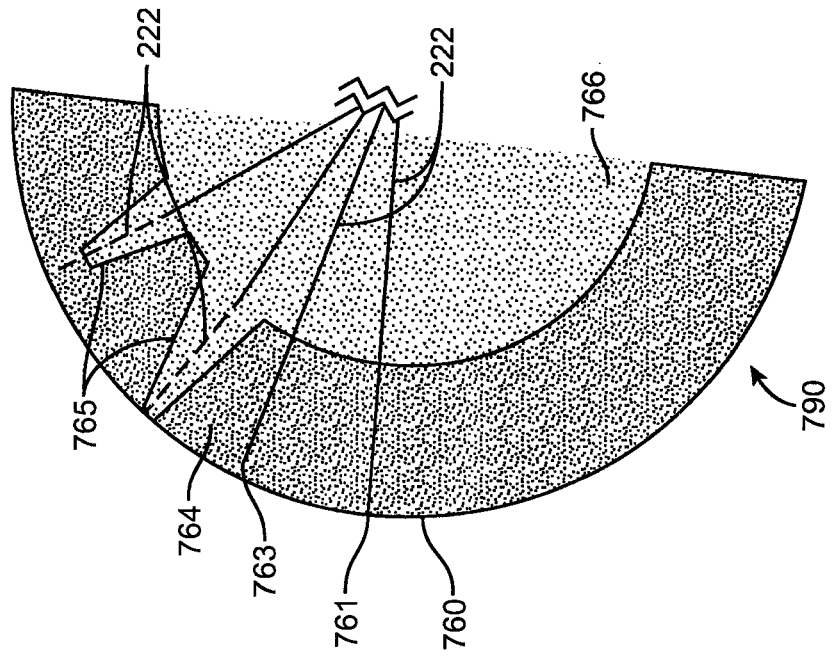
FIGS. 7A-7B illustrate location and orientation of the elongate elements of the second conductor incorporated in a structure with a convex surface, layer, or thickness over a volume.
Figure 7A:
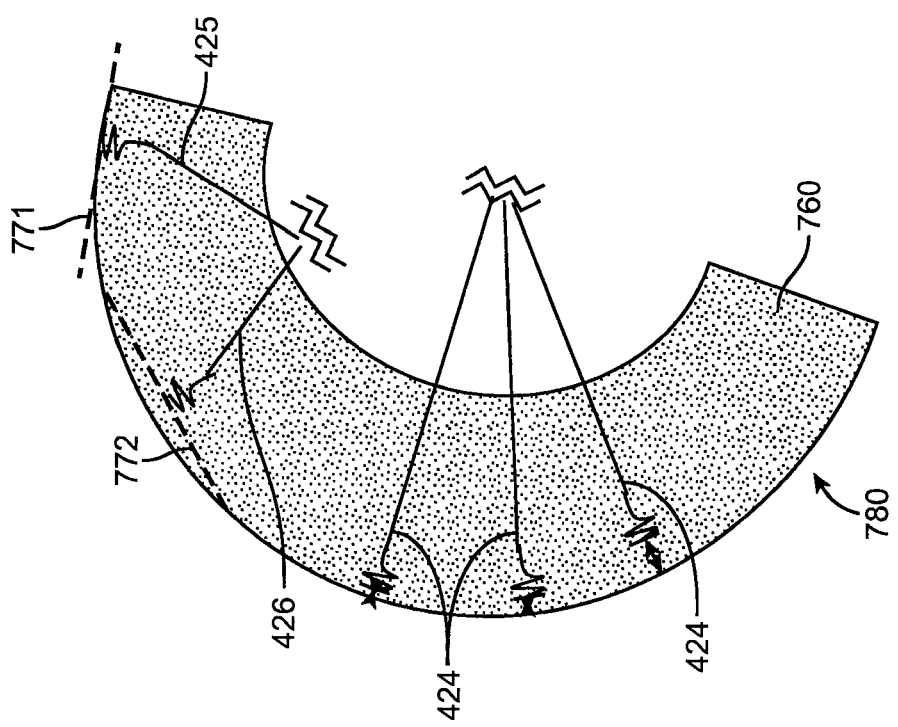

FIGS. 7A-7B depict location and orientation of the elongate elements of the second conductor in a cross sectional view with the principles described above in a structure with a convex surface, layer, or thickness. In a structure having a hollow volume 780, such as an enclosure or luminal structure, the detection portion of the conductors 424 shown in loops terminate distally at different depths below the surface, layer, or thickness to be monitored. With conductors 425 and 426, the spiral ends transect tangential planes 771 at the full thickness of the surface and 772 at an even deeper layer in the core of the structure, respectively. Regardless of the angle of approach, it is readily seen that the longitudinal axis of the elongate element transects a plane of the convex surface, layer, or thickness subject to breach. Shown with the volume comprising a solid cored structure 790, the conductors 222 are placed with their longitudinal axes radiating from the core toward the surface, layer, or thickness to be monitored 760 ending at partial thickness 761 and full thickness 763. In structures that are heterogeneous, shown here as biphasic with material 764 concentrically wrapped around a core material 766, it may be advantageous to have the core material form optional projections or protuberances here shown as cones 764 and 765 around the conductors. The alternating peaks and valleys of the two materials dovetail to provide mechanical stability to prevent delamination and/or hinder shearing forces at the interface that could tear the conductor and compromise its integrity.

Figure 8:
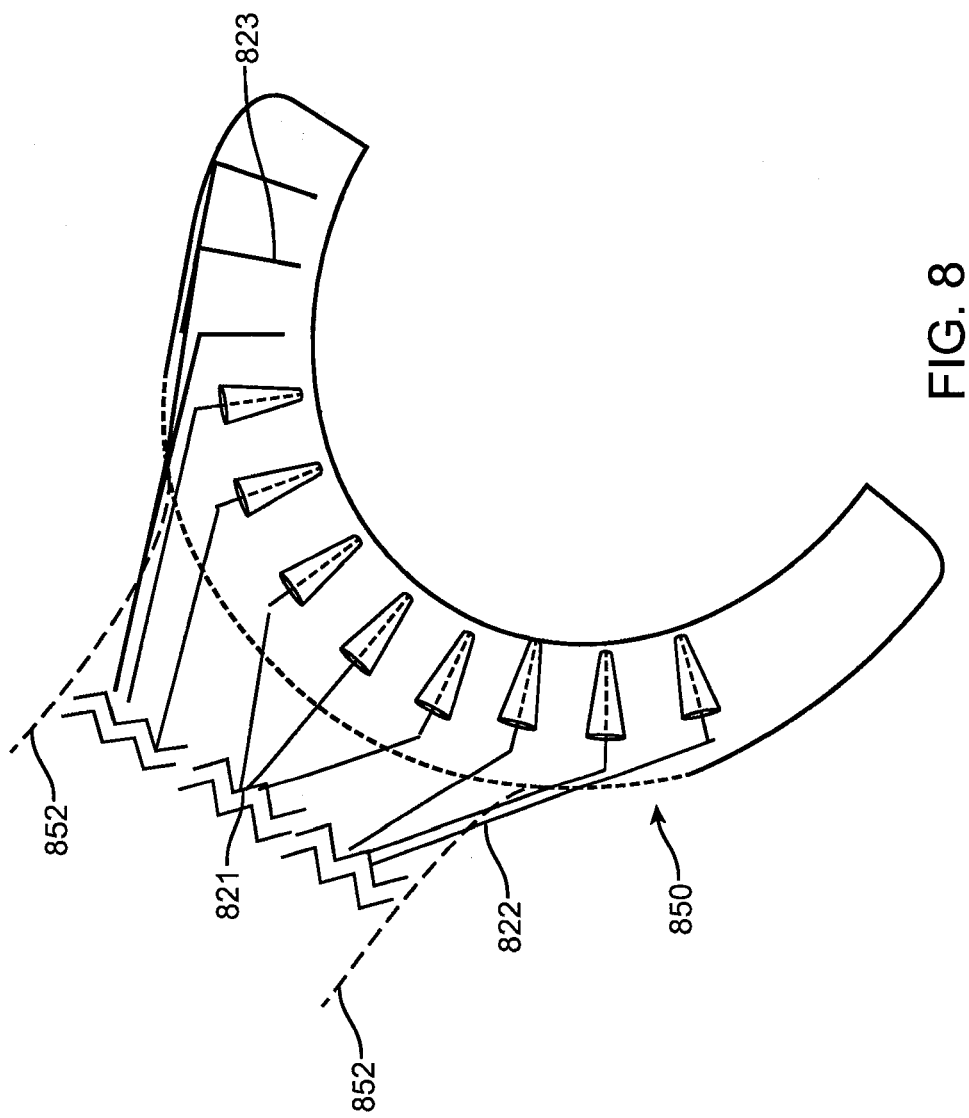
FIGS. 8 and 9 illustrate location and orientation of the elongate elements of the second conductor incorporated in a structure with a concave surface, layer, or thickness.
Figure 9:
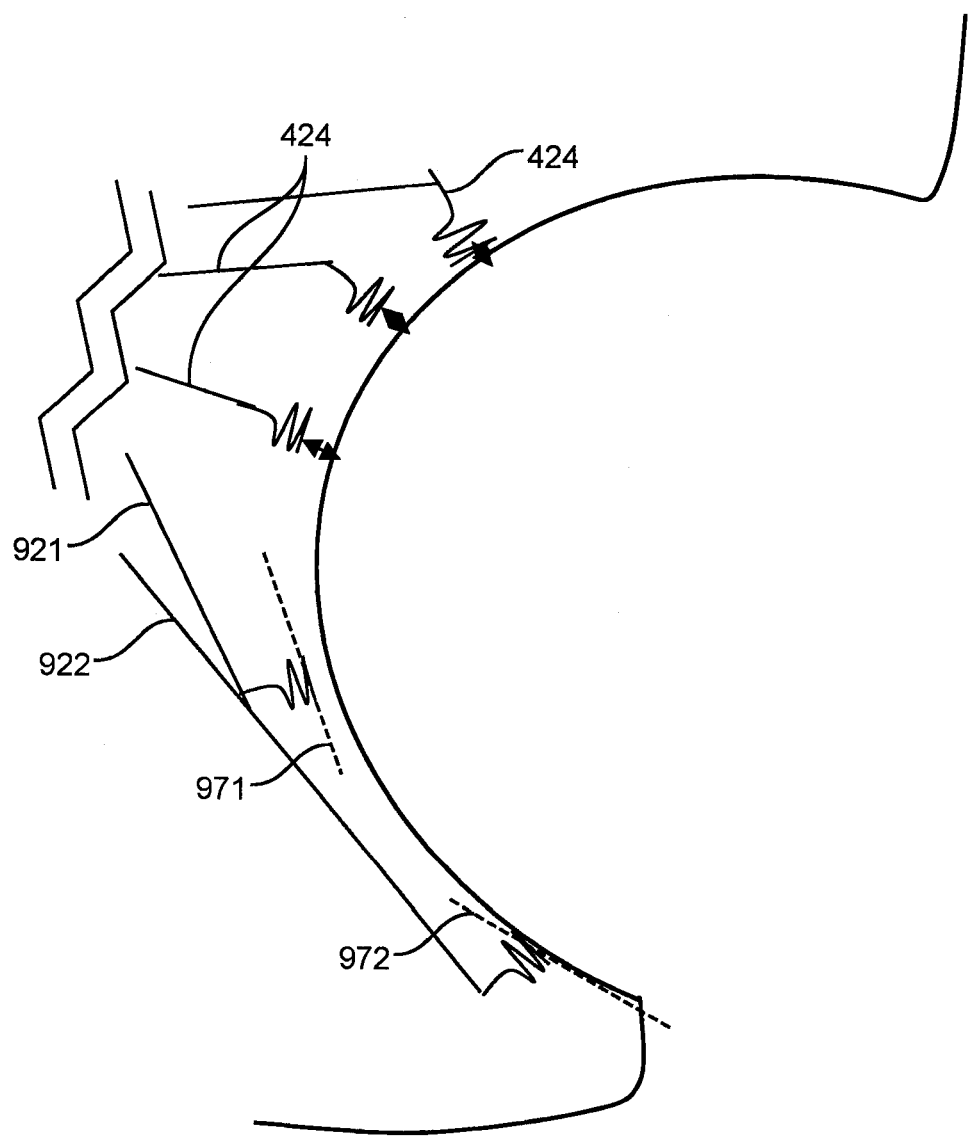

FIGS. 8 and 9 depict location and orientation of the elongate elements of the second conductor in a cross sectional view with the principles described above in a structure with a concave surface, layer, or thickness. The base of the structure 850 is partial and curved in dotted lines for a fastening mechanism to immobilize the component, such as a device housing, to the body. An optional configuration where it is narrowed and/or extended to form a neck 852 for the connection is shown in dashed lines. Alternatively, the concave structure, such as a luminal enclosure or connector component, is fastened to another part of the device. The detection portions of the conductors 821 and 822 radiate distally toward the core of the concavity and terminate in different layers of the structure. They may be combined either singly or grouped in a staggered array (not shown). Conductor 823 has a multi-pronged formation of elongate elements aimed toward the concavity in the direction of the breach. The conductors typically extend proximally through the structure and drape along the back to reach and connect to the logic circuit, which can be placed in a variety of locations. In FIG. 9, the base of the concave surface, layer, or thickness is wide and extend to cover its entirety in an optional configuration. Conductors 424 are shown with a spiral configuration with termination distally at various depths. Tangential planes 971 at the full thickness of the surface and 972 at an even deeper layer are transected by their respective conductors, 921 and 922. Regardless of the angle of approach, it is readily seen that the longitudinal axis of the elongate element transects a plane of the concave surface, layer, or thickness subject to breach.

Figure 10B:
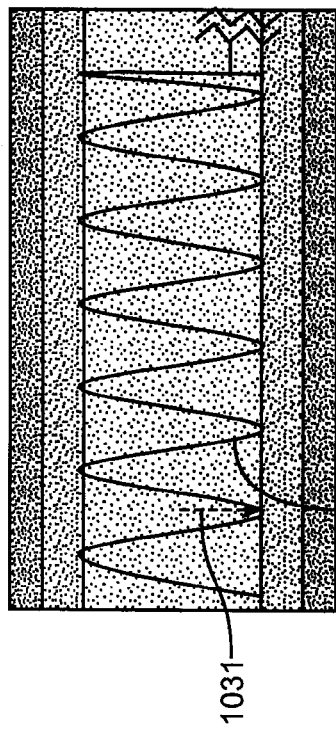
FIGS. 10A-10C illustrate another configuration where the elongate is a long spiral, coil, or helix.
Figure 10C:
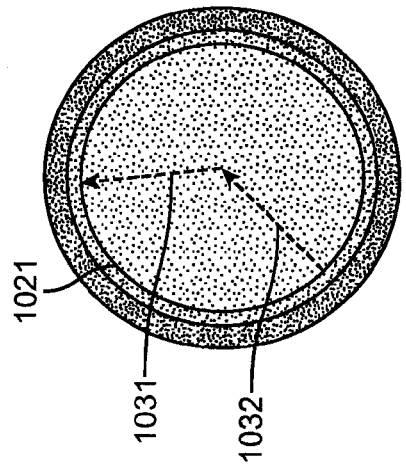
Figure 10A:
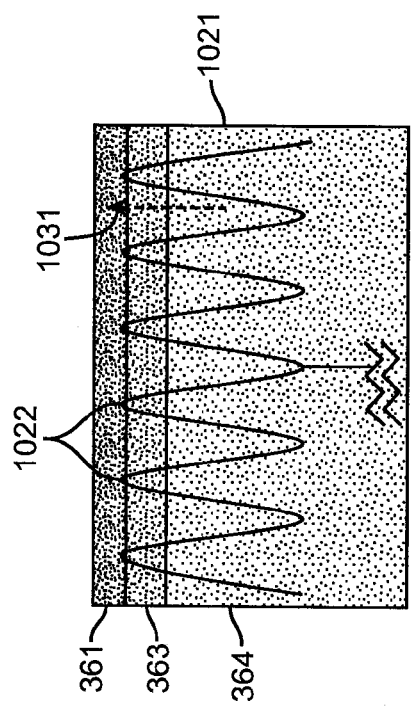
Figure 11B:
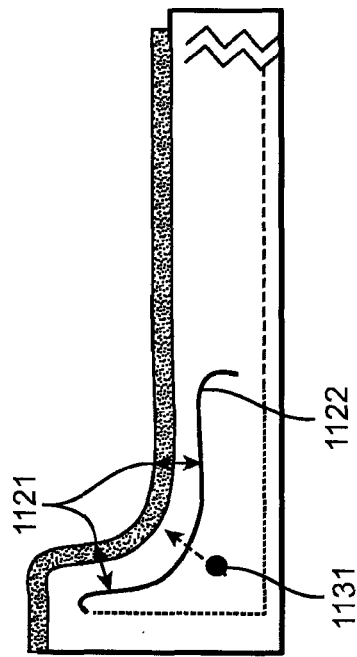
FIGS. 11A-11D illustrate how a loop or coil configuration of the elongate element is incorporated in more complex surfaces, layers, or thicknesses.
Figure 11D:
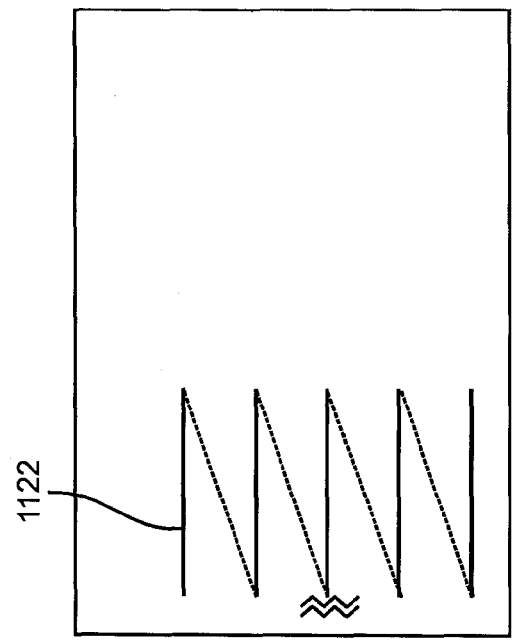
Figure 11A:
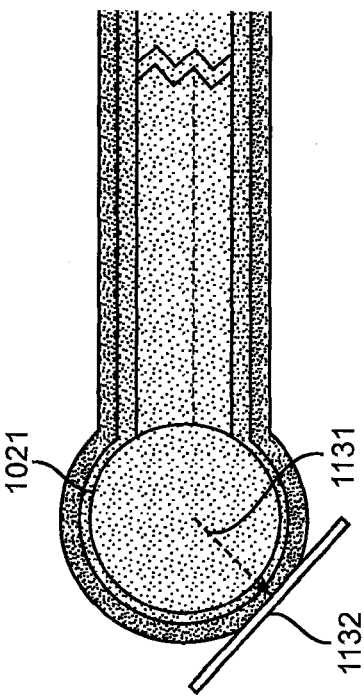
Figure 11C:
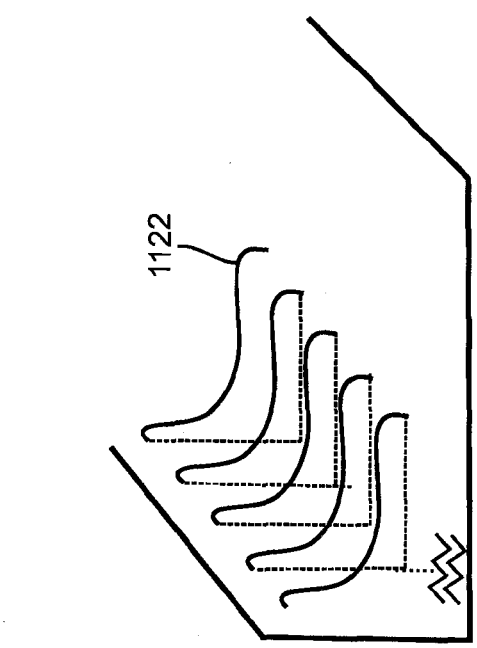

Referring now to FIGS. 10A-10C show where the elongate element 1021 is in the continuous loop configuration of a long spiral, coil, or helix with radial axes 1031 oriented toward the direction of a surface, layer, or thickness subject to breach. In this configuration, the conductor seen from the top (not shown) presents at the desired depth an electrically conductive discontinuous line or curve of dots and/or dashes formed by the peaks 1022 to detect the breach. In a longitudinal sectional view (FIG. 10B) and a cross sectional view (FIG. 10C), this configuration will enable detection over a cylindrical surface with a single conductor. This configuration (FIG. 10C) also enables detection of an internal breach, for example a breach of a concave surface or layer of a housing or luminal structure, initiated in the internal core volume that propagates laterally toward the surface with the radial axis 1032 directed inward.

In FIGS. 11A-11D, how this loop or coil configuration of the elongate element can be applied to surfaces, layers, or thicknesses with more complex contours or silhouettes is shown. In the sectional view FIG. 11A, the detection portion 1021 of the coil presents an electrically conductive spiral to detect a breach in a protuberant or thickened edge commonly used to reinforce and increase durability of an edge, for example, a leaflet of a cardiovascular valve. The radial axis 1131 of the elongate element is shown intersecting the tangential plane 1132 of the surface, layer, or thickness. Surfaces having a mixture of flats, protuberances, and indentations like many naturally occurring in the body, such as joint articular surfaces, are shown from a simplified cross sectional view in FIG. 11B, projectional view in FIG. 11C, and a top view in FIG. 11D. Using the mold for the part, the conductor 1122 can be formed, bent, and wound into shapes that faithfully follow the contour so that it is equidistant at two or more points 1121 along its length closest to the surface, layer, or thickness subject to breach. The shallower portions of the conductor, here shown in a continuous line in FIGS. 11B, 11C, and 11D, form conductive curves projecting to the direction of the breach and are oriented to the contour of the surface, layer, or thickness. In all these configurations, the connection to the circuitry is in a deep, protected part of the device and oriented away from the area prone to the breach.

FIGS. 12A-12C, 13A, 13B, 14A-14C, 15A, 15B, 16A, 16B, 17A, 17B, 18A-18D, and 19, illustrate how the breach detection system is deployed in various exemplar applications in orthopedic prosthesis, the hip, a simple ball and socket joint, and the knee, a highly complex joint, encompassing most, if not all, of the types of motions and forces a joint experiences while static or in motion. It will be appreciated that the applications are not limited to these two joints and can be similarly applicable to unicompartmental knee joints and other joints or partial joints in the body. It will further be appreciated that configurations of the elongate elements described in the other figures above, while not shown here, can be deployed in the fashion described to suit the situation. The teachings will be applicable to naturally occurring, synthetic, biologically derived, or hybrid materials used in such devices including but not limited to metal alloys, polymers, ceramics, and biologics, and in articulating contacts whether metal-to-metal, metal-to-polymer, metal-to-ceramic, polymer-to-ceramic, polymer-to-polymer, ceramic-to-ceramic, and to their biologic equivalents and hybrids.

Figure 12B:
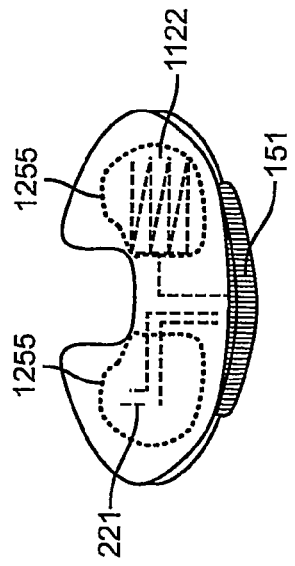
FIGS. 12A-12C illustrate a knee prosthesis having the breach detection system of the present invention incorporated in the components on the tibial side.
Figure 12C:
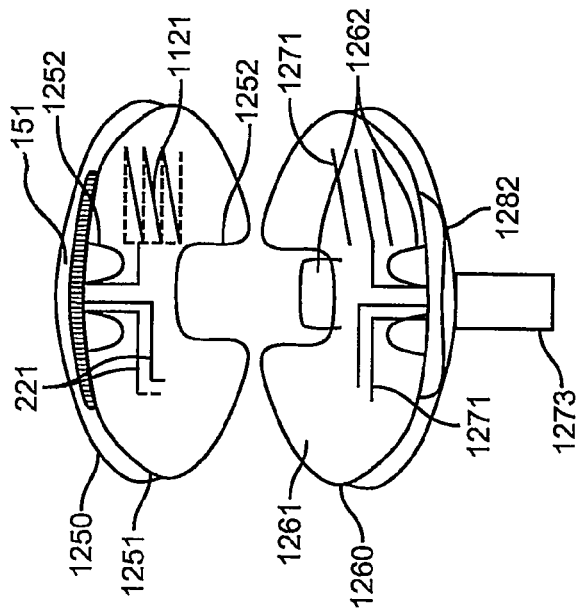
Figure 12A:
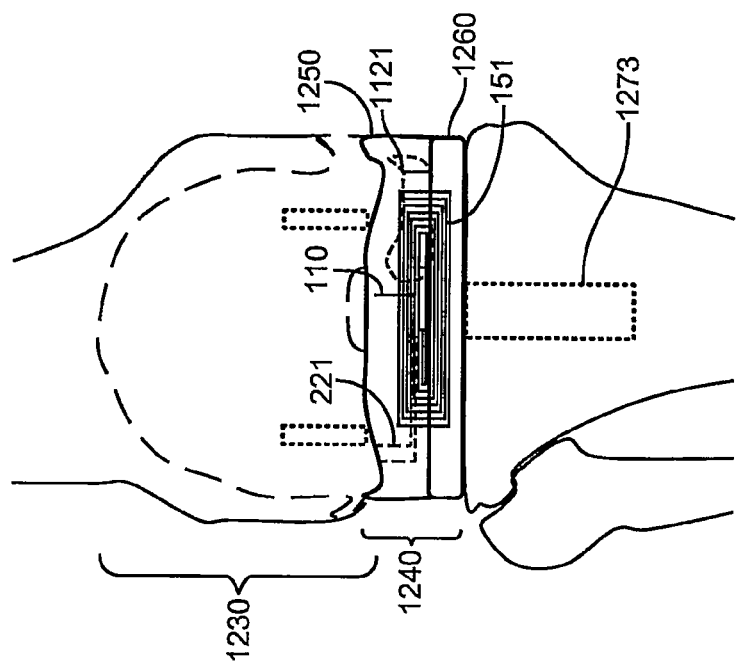
Figure 14B:
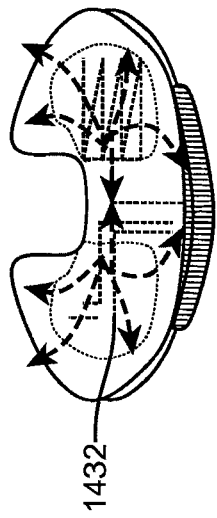
FIGS. 14A-14C illustrate the various wear and tear forces that the knee experiences during stances and movements leading to a breach of a surface, layer, or thickness.
Figure 14C:
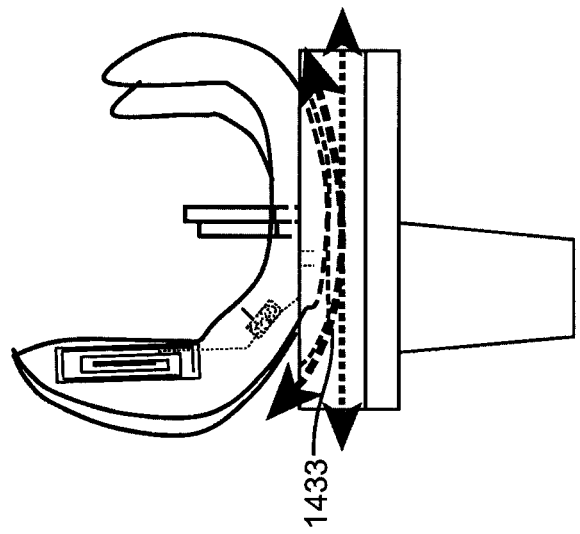
Figure 14A:
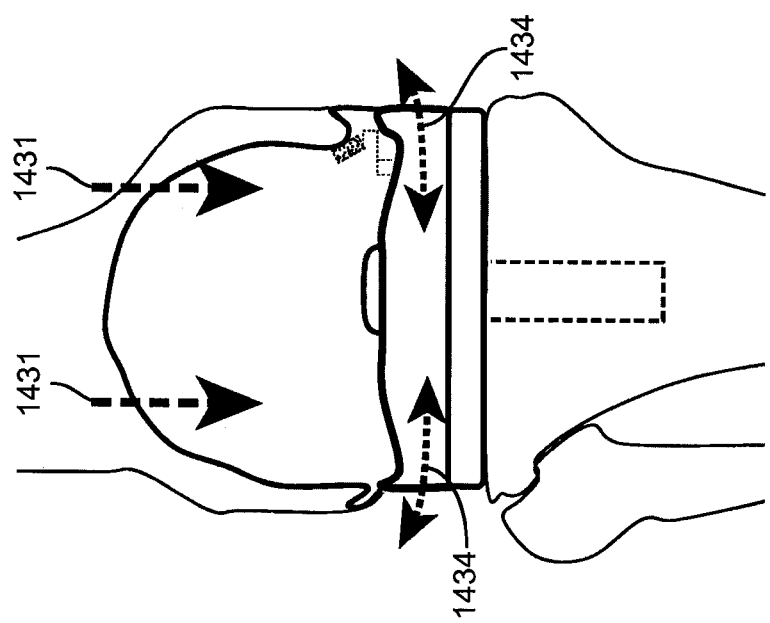
Figure 15A:
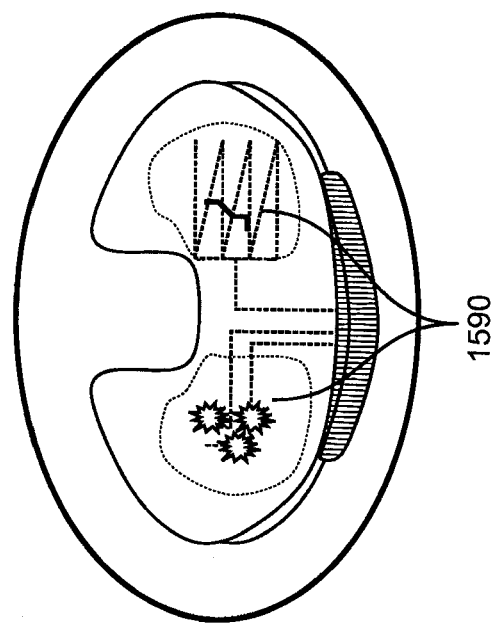
FIGS. 15A-15B illustrate the operation of the passive transponder detection system in the knee prosthesis with a handheld reader.
Figure 15B:
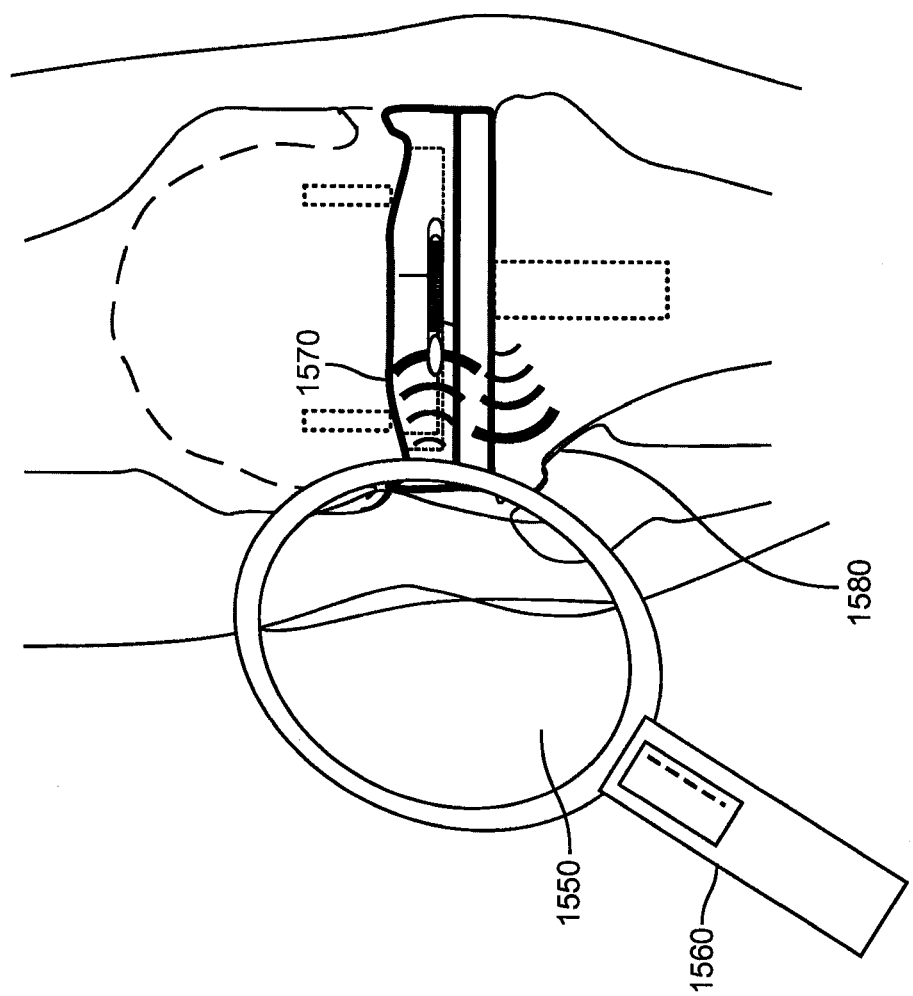

FIGS. 12A-12C, 13A, 13B, 14A-14C, 15A and 15B show deployment in the total knee replacement joint comprising two components, the femoral 1230 and the tibial 1240. The patellar component is not shown here as it is not load bearing but the teachings can similarly apply. The tibial component itself typically comprises two parts, an articulating plate or insert 1250 above and a support plate 1260 below as shown in FIGS. 12A and 12B. The femoral component sits on the contoured superior surface of the tibial articulating plate as shown in FIGS. 13A and 13B. FIGS. 14A-14C depict the variety of wear and tear forces that the joint experiences during different stances and movements. In FIGS. 15A and 15B, the operation of the system is depicted. The tibial articulating plate is described in these teachings as made of polymer, such as ultra high density polyethylene, but can be made of any biocompatible material. While the system is not shown embedded in the tibial support plate, the teachings can be similarly applied. The tibial support plate is typically made of alloy and separated from the hostile conditions by the articular plate, which bears the brunt of the wear and tear. Thus, no meaningful wear and tear to this part is anticipated unless the damage to the articulating insert extends far beyond what is detectable. Note that the teachings will be applicable to partial deployment or replacement of only a part, a component, a single articulation, or a combination thereof.

Referring now to FIG. 12A, the tibial component is anchored and fixated inferiorly with a post 1273 to the surgically truncated tibia. The circuit and antenna 151 and a first conductor 110 on a shielded substrate are fixated away from articulating and radiofrequency disadvantaged areas, here placed in an exterior facing area on the anterior surface, of the polymer articulating plate. The polymer plate 1250 with the circuitry 151 fit on top of the adjoining area in the alloy plate 1282. Optionally, the anterior surfaces of the plates adjacent to the substrate can be undercut, as shown here, in order to form a smooth contour over the anterior surface of the tibial component. The plane of the antenna is relatively in parallel to the surface of the overlying tissues and skin on the anterior part of the knee. In this location, the incoming radiofrequency signals are relatively free from interference by the metallic components, which are behind the antenna and shielding. FIG. 12B shows the superior articular surface of the polymer plate, the concave area of articulation in contact with the femoral component 1255 in dotted lines, and two configurations of the second conductors 221 and 1122 embedded below. In FIG. 12C, the two plates are disassembled like a clamshell. The inferior surface of the polymer plate 1251 mates with the superior surface of the alloy plate 1261, commonly with female 1252 and male 1262 mechanisms as anchors. While shown near the center of the component, one or more of the fastening mechanisms can be placed at any suitable location. These interlocking mechanisms are preferably non-destructive on the alloy plate side in the removal of only the polymer plate to facilitate the replacement of a worn polymer plate with a new one. Using this method of replacing only the worn part without replacement of the intact alloy plate would simplify the procedure and spare unnecessary bone loss. Two different arrangements of the second conductors are deployed in exemplar fashion. Second conductors 221 isolated from each other run from the logic circuit along the inferior surface of the polymer plate, penetrate through at the desired points, and terminate at the desired depths behind the superior articulating surface. In this configuration, two depths of breach can be detected. Second conductor 1122 runs from the logic circuit along the inferior surface of the polymer plate, penetrates through at the desired point, and forms or connects to a continuous coil of a complex shape with points along its length equidistant in depth from the articulation contact area on the superior surface. In this configuration, the coverage area for the breach of the same depth over the articulation contact area, an uneven contour, is enlarged with a single conductor. Optional additional grooves 1271 or sunken areas can be undercut on the superior surface of the alloy plate to accommodate the section of the second conductor on the inferior surface of the polymer plate. Alternatively, the circuitry can be designed as a package or have its own interlocking mechanisms to fit securely onto either or both plates (not shown). The entire circuitry could be further attached, encased, or hermetically sealed to the polymer plate on its inferior, non-articular, surface in protective material to form one fixed, solid piece, if desired. Alternatively, the polymer insert may be constructed in two or more pieces, medial and lateral, each with its own conductors and circuitry (not shown). In this configuration, each side can be monitored and, when impairment detected, replaced independent of each other.

The system incorporated in the femoral component 1230, which sits on the tibial component 1240, in anterior and side views, FIGS. 13A and 13B, respectively. The femoral component is fitted to the surgically shaved femoral head and anchored with posts 1360. The logic circuit 130 and first conductor 110 is fixated away from articulating areas, here on the shielded interior side wall of the component. The antenna 140 on a shielded substrate is fixated away from articulating and radiofrequency disadvantaged areas, here on the exterolateral side of the component and its plane relatively in parallel to the surface of the overlying tissues and skin. In these locations, the incoming radiofrequency signals are relatively free from interference by the metallic components, which are beneath the antenna. In addition, the plane of the antenna is relatively orthogonal to the radiofrequency vector thereby maximizing the capture of radiofrequency energy and strength of signal. Referring now to FIG. 13B, a lead runs from the antenna, either penetrates the side wall at a desired point or cross over the edge, along the interior side wall to connect electrically to the logic circuit. A second conductor 622 of the double prong configuration is shown. Each prong is embedded in the desired depth and aimed toward the articulation contact area of the femoral component 1380, runs away from the articulating surface subject to breach, emerges out of the floor, joins the other prong, runs along the floor and interior side wall to connect electrically with the logic circuit. In this configuration, two pinpoint areas, whether close or far, subject to breach could be monitored simultaneously by one conductor. Again, the entire circuitry could be further attached, encased, or hermetically sealed to the assembled femoral component in protective material to form one solid piece, if needed.

In FIGS. 14A-14C, a selection of the various wear and tear forces encountered by the knee are depicted with the articular planes of the components transecting the load bearing axis. In a stationary position, a load or impact 1431 is directly delivered by the most distal portions of the femoral component causing compression and dispersion forces 1432 on articulating contact areas, esp. that of the polymer plate. A change in stance would shift the load and center of such forces to other areas while its axis is still transected by the articular planes. Rotation, abduction and adduction, would cause corresponding shearing forces and load shifts in the same direction 1434. Flexion and extension causes a mixture of rotational and frictional forces 1433.

FIGS. 15A-15B shows the progression of the accrued wear and tear resulting in pitting and cracking in the softer polymer plate 1590 thereby exposing the embedded second conductor in the breach. Interstitial fluid enters the breach and the ions electrically bridge the second conductor with the exposed first conductor enabling the logic circuit to send a breach signal. During examination of the device, a radiofrequency reader 1550 is held over the hermetically sealed capsule containing the circuit and antenna and an interrogation signal is sent 1570 and a signal 1580 indicating "breach" or "no breach" is returned and shown on the display panel 1560. Depending on the configurations of the embedded second conductors, partial breach, breach location, and the extent of the breach could be detected and displayed. If the wear and tear can be detected early, prior to any degradation of the underlying alloy plate or the femoral component, the impaired polymer plate can then be replaced in a relatively minor procedure without replacing the tibially fixated alloy plate, thereby sparing the bone tissue.

Figure 16B:
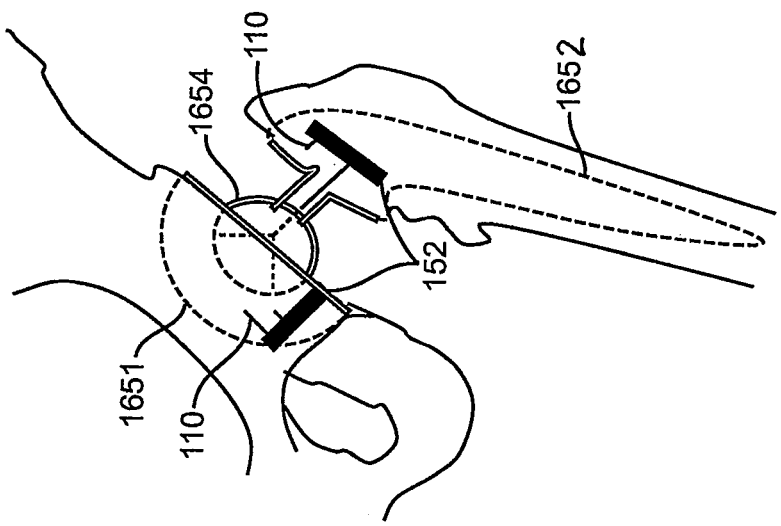
FIGS. 16A-16B illustrate the various wear and tear forces that the hip experiences during stances and movements leading to a breach of a surface, layer, or thickness and a hip prosthesis having the breach detection system of the present invention incorporated herein.
Figure 16A:
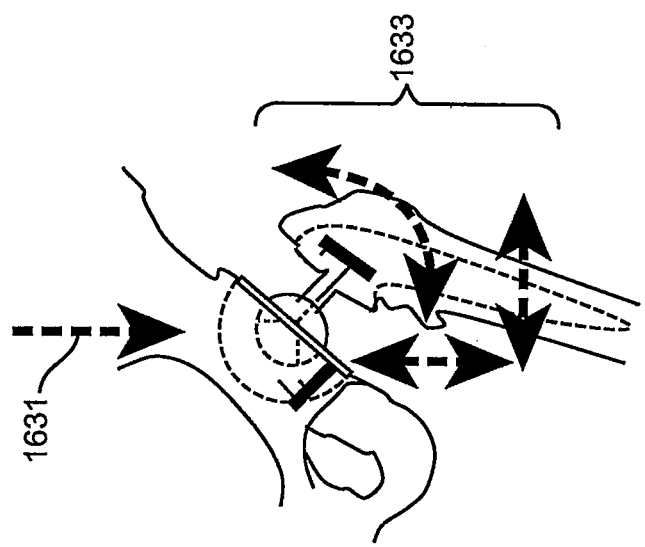

In FIGS. 16A-16B, a selection of the various wear and tear forces encountered by the hip are depicted and the system is shown deployed in the total hip replacement joint comprising two components, the acetabular 1651 and the femoral 1652. In a stationary position, a load or impact 1631 is directly delivered by the femoral head causing compression and dispersion forces (not shown) on articulating contact areas, esp. that of the polymer liner. A change in stance would shift the load and pressure point of such forces to other areas in the liner. Rotation, abduction, adduction, flexion, and extension 1633 would cause corresponding shearing and frictional forces in the same direction. Normal movement of the leg is a mixture of these actions and would result in a combination of these forces in various degrees affecting both the acetabular liner and the femoral component. The logic circuits and their respective antennas 152 and the first conductors 110 are shown oriented toward the outside of the body, typically in an antero-medial or postero-lateral direction with the planes of the antenna fixated relatively in parallel to the surface of the overlying tissues and skin. The logic circuits, antennas, and first conductors are fastened to an external and radiofrequency advantaged area on the respective components or on the bone in which the respective components are anchored. In these locations, the incoming radiofrequency signals are relatively free from interference from the metallic components, which are behind the antenna. In addition, the plane of the antenna can be orthogonal to the radiofrequency vector in order to maximize transmission signal strength and capture of radiofrequency energy.

Figures 17A, 17B:
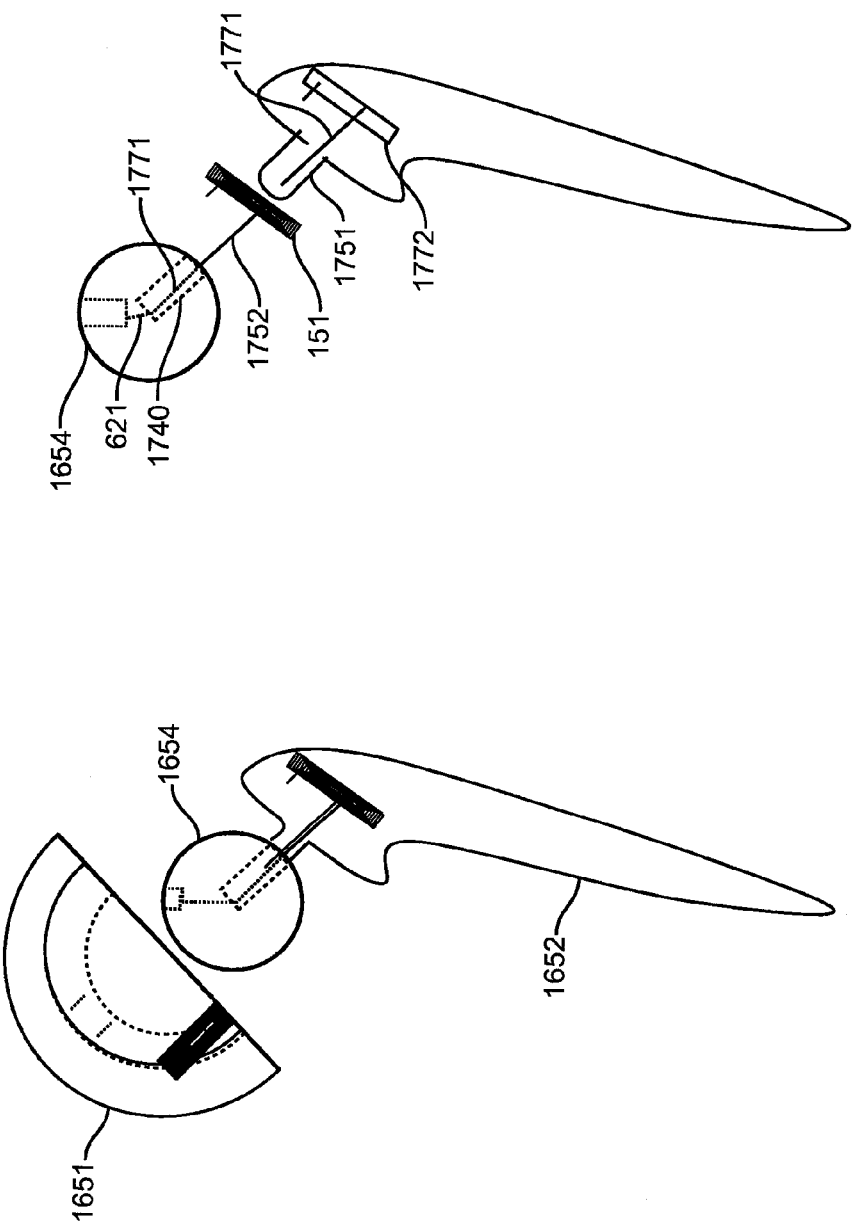
FIGS. 17A-17B illustrate a hip prosthesis having the breach detection system of the present invention incorporated in the femoral head component.
Figure 18A:
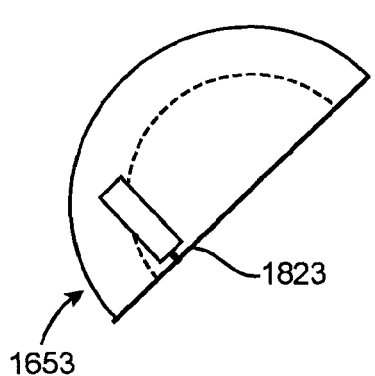
FIGS. 18A-18D illustrate a hip prosthesis having the breach detection system of the present invention incorporated in the acetabular cup component.
Figure 18C:
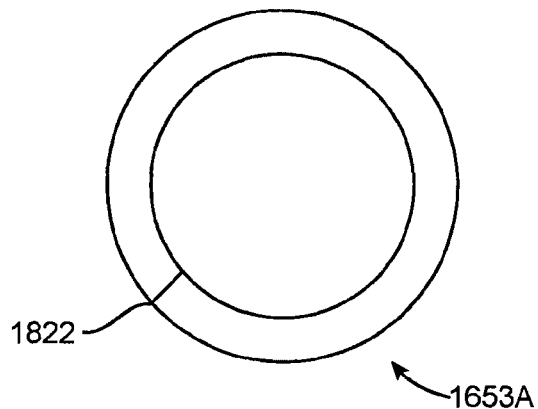
Figure 18B:
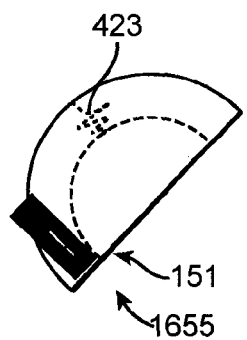
Figure 18D:
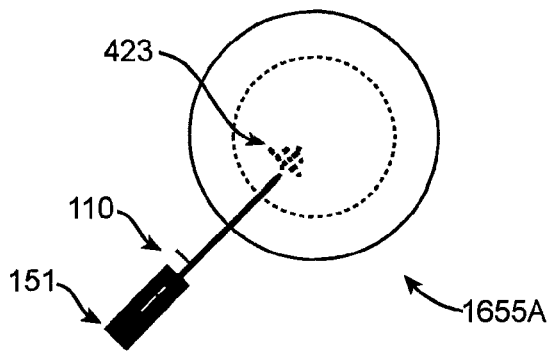

The two disarticulated components and the disassembled femoral component are shown in FIGS. 17A-17B. FIG. 17A shows how the spherical head fits in the hemispherical cup of the acetabular component. As shown in FIG. 17B, the femoral component typically comprises two parts, a spherical alloy head 1654 with a cylindrical orifice 1740 into which the neck of the alloy femoral shaft 1751 is inserted. A double pronged second conductor 621 is embedded with its tips at the predetermined depth in the head projected outward. The prongs connect electrically in a lead 1752, which emerges into the cylindrical orifice and runs along its interior wall and out of the head to connect to the logic circuit. Optionally, the circuitry could be further attached, encased, or hermetically sealed to the femoral head in protective material to form one fixed, solid piece, if needed. Grooves 1771 can be undercut either on the interior wall of the orifice or on the neck of the femoral shaft to fit the lead. The area for the logic circuit, antenna, and first conductor 151 is undercut 1772 to fit the circuitry in order for the femoral shaft to have a smooth, continuous contour. Alternatively, not shown here, the circuitry is attached to tissue that moves coterminously with the femoral head and shaft, so that it is not dislocated or torn by movement of the body.

FIGS. 18A-18D depicts the deployment of the system in the acetabular component. The alloy acetabular cup viewed from the side 1653 and front 1653A are shown. A liner, commonly made of polymer, such as ultra high density polyethylene, but could be any kind of suitable material, viewed from the side 1655 and from the back 1655A are shown. A spiral second conductor 423, embedded at a specified depth from and oriented toward the concavity of the liner 1655, runs outward, emerges from the liner, runs along the convex posterior wall to connect with the logic circuit and antenna on a substrate 151. When the liner is fixated to the acetabular cup by anchors, the logic circuitry is draped over the exterior of the cup. As analogous to the knee prosthesis, these interlocking anchors are preferably non-destructive on the alloy liner side in the removal of only the polymer liner to facilitate the replacement of a worn liner with a new one. The locations of these fastening mechanisms can be placed at any suitable location so long as the device can function properly. Using this method of replacing only the worn part without replacement of the intact alloy cup would simplify the procedure and spare unnecessary bone loss. A slot on the edge of the cup 1822 and an area on the exterior of the cup 1823 can optionally be undercut such that the lead extension and circuitry could be inserted in place and fastened. Alternatively, the circuitry could be fastened to a wing on the acetabular cup (not shown) or the side of the pubic bone. In the case where the acetabular component is a singular piece, the second conductor can be embedded in the same fashion as the liner, emerges from the liner in the back, runs along the convex posterior wall to connect with the logic circuit and antenna 151. In this configuration, the circuitry could be fastened to the exterior wall of or a wing on the acetabular cup or the side of the pubic bone. Optionally, the circuitry could be further shielded, attached, encased, or hermetically sealed to the acetabular liner and/or cup in protective material to form one solid piece, if needed. While they are not shown here, it will be appreciated that the circuitry can be designed by one skilled in the art as a package with fixating mechanisms in a myriad of ways to fit securely onto the device.

Figure 19:
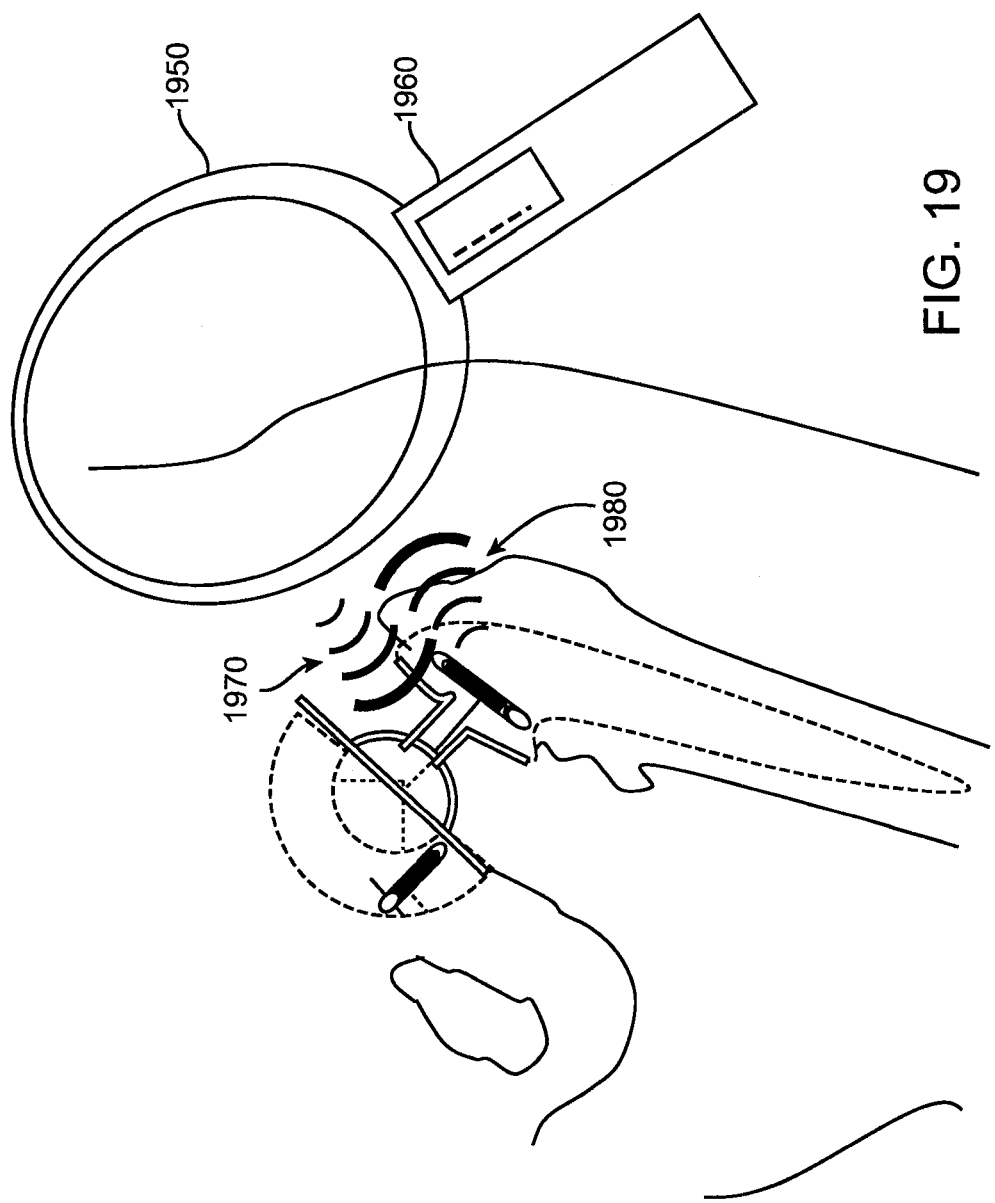
FIG. 19 illustrates the operation of the passive transponder detection system in the hip prosthesis with a handheld reader.

FIG. 19 shows the system in operation, here with a hermetically encapsulated device with a ferrite core antenna. As in the knee, the progression of the accrued wear and tear resulting in pitting and cracking in the softer acetabular liner exposes the embedded second conductor in the breach to the surrounding interstitial fluid. Naturally occurring ions in the interstitial fluid enters the breach electrically connect the exposed conductor with the exposed first conductor enabling the logic circuit to send a breach signal. During examination of the device, a radiofrequency reader 1950 is held over the antenna of the selected component and an interrogation signal is sent 1970 and a signal 1980 indicating "breach" or "no breach" is returned and shown on the display panel 1960.

Each logic circuitry will have an identifying code to indicate which component, if any, or both have been breached. Depending on the configurations of the embedded second conductors, partial breach, breach location, and the extent of the breach could be detected and displayed. If the wear and tear can be detected early, prior to any degradation of the alloy acetabular cup or the femoral head, only the impaired liner is then replaced in a relatively minor procedure, thereby sparing the bone tissue.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. An implantable device comprising:
   a solid structure having a load-bearing surface over a volume, said surface being subject to wear;
   a first electrical conductor located internally or externally of the solid structure;
   an electrically conductive array including one or more elongate conductive elements embedded in the volume of the solid structure and isolated from said first electrical conductor, wherein said conductive elongate elements project in a direction from an interior of the volume toward a region on the load-bearing surface; and
   wireless signaling circuitry coupled between the first electrical conductor and the electrically conductive array so that an electrically conductive fluid surrounding the solid structure electrically bridges the first electrical conductor and the electrically conductive array to enable the circuitry to emit a detectable wireless signal warning when the load-bearing surface wears down sufficiently to expose at least one distal portion of one or more of the conductive elongate elements.

2. An implantable device as in claim 1, wherein the elongate conductive elements are generally linear.

3. An implantable device as in claim 1, wherein the elongate conductive elements comprise a serpentine structure.

4. An implantable device as in claim 1, wherein the elongate conductive elements form a helix.

5. An implantable device as in claim 1, wherein the elongate conductive elements have distal, spiral tips.

6. An implantable device as in claim 1, wherein a major axis of the said elongate elements intersects a planar region of the external surface subject to wear.

7. An implantable device as in claim 6, wherein the major axis intersects the planar region of the external surface at an angle in the range from 60° to 90°.

8. An implantable device as in claim 1, wherein the electrically conductive array comprises a loop with detection portions equidistant at two or more points along its length closest to the surface subject to wear constituting an electrically conductive linear or curved pattern following the contours of the surface.

9. An implantable device as in claim 1, wherein the volume of the device comprises an articular component of an orthopedic implant.

10. An implantable device as in claim 1, wherein bridging of the electrically conductive elements energizes the circuitry, closes the circuitry or opens the circuitry to cause, alter, disable, or enable signal emission.

11. An implantable device as in claim 10, wherein the electrically conductive elements are spaced-apart and are electrically coupled to close and/or alter a capacitance or inductance of the signaling circuitry when exposed to an electrically conductive fluid.

12. An implantable device as in claim 10, wherein the electrically conductive elements conduct electrical current when exposed to electrically conductive fluids by wear.

13. An implantable device as in claim 10, wherein the signaling circuitry comprises a transponder and an antenna, wherein the transponder is powered by an external reader which is tuned to the antenna of the transponder, wherein the transponder and antenna are inactive or operational in a first mode until wear permits fluid intrusion which activates or alters the transponder emission.

14. An implantable device as in claim 1, wherein the electrically conductive element comprises a pharmacologic agent.

15. An implantable device as in claim 1, wherein the electrically conductive array carries a pharmacologic agent exposed by the wear.

16. An implantable device as in claim 14, wherein the pharmacologic agent resides with the conductive element.

17. An implantable device as in claim 14, wherein the pharmacologic agent resides in the non-conductive covering.

18. A method for signaling breach of a solid structure of an orthopedic device having a load-bearing surface implanted in a body, said method comprising:
    coupling an array of one or more elongate conductive elements embedded in a volume of the solid structure to an electrical conductor located internally or externally on the device, wherein said elongate conductive elements project in a direction from an interior of the volume of the structure toward the surface of the structure of the device wherein the elongate elements are electrically isolated from the internal/external conductive element;
    implanting the solid structure into body tissues so that the external surface is exposed to body fluids, wherein the load-bearing surface wears down over time; and
    emitting an externally detectable wireless signal when the said surface has worn sufficiently to expose at least one distal portion of one or more of the elongate conductive elements to the body fluids to bridge the internal/external electrical conductor and said one or more of the elongate conductive elements to close a circuit to enable or cause emission of said signal.

19. A method as in claim 18, wherein the signaling circuitry is unpowered and comprises an antenna and a transponder, further comprising directing an interrogation signal to the antenna and detecting a return signal from the transponder, wherein the returned signal is altered, present or ceases only when the conductive elements have been bridged by wear.

20. A method as in claim 18, wherein the signaling circuitry is powered and emitting comprises exposing a component of a signaling circuit to an internal or external environment when the surface is at least partially breached wherein the signaling circuit is closed and transmits a signal.

21. A method as in claim 18, wherein the device comprises an artificial joint.

22. A method as in claim 21, wherein the said wireless signal indicates dysfunction or impending dysfunction of the device and facilitates timely replacement of only an impaired part or component.

* * * * *